US 9,248,178 B2

(12) United States Patent
Kang et al.

(10) Patent No.: US 9,248,178 B2
(45) Date of Patent: Feb. 2, 2016

(54) DIFFERENT SEROTYPES OF VESICULAR STOMATITIS VIRUS AS EXPRESSION VECTORS FOR IMMUNIZATION REGIMENS

(76) Inventors: Chil-Yong Kang, London (CA); Gyoung Nyoun Kim, London (CA)

(*) Notice: Subject to any disclaimer, the term of this patent is extended or adjusted under 35 U.S.C. 154(b) by 616 days.

(21) Appl. No.: 13/376,875

(22) PCT Filed: Jun. 8, 2010

(86) PCT No.: PCT/CA2010/000874
§ 371 (c)(1), (2), (4) Date: Jan. 5, 2012

(87) PCT Pub. No.: WO2010/142030
PCT Pub. Date: Dec. 16, 2010

(65) Prior Publication Data
US 2012/0100176 A1    Apr. 26, 2012

Related U.S. Application Data

(60) Provisional application No. 61/184,959, filed on Jun. 8, 2009.

(51) Int. Cl.
A61K 39/12     (2006.01)
A61K 39/205    (2006.01)
C12N 7/00      (2006.01)
C12N 15/86     (2006.01)
A61K 39/00     (2006.01)

(52) U.S. Cl.
CPC ............ *A61K 39/205* (2013.01); *A61K 39/12* (2013.01); *A61K 2039/5256* (2013.01); *A61K 2039/545* (2013.01); *C12N 7/00* (2013.01); *C12N 15/86* (2013.01); *C12N 2740/12043* (2013.01); *C12N 2760/20234* (2013.01); *C12N 2760/20243* (2013.01); *C12N 2770/24234* (2013.01); *C12N 2810/6081* (2013.01)

(58) Field of Classification Search
None
See application file for complete search history.

(56) References Cited

U.S. PATENT DOCUMENTS

2006/0193872 A1    8/2006  Jones et al.
2009/0162321 A1    6/2009  Parks et al.

FOREIGN PATENT DOCUMENTS

CA    2520279 A1       10/2004
WO    2004093906 A1    11/2004

OTHER PUBLICATIONS

Rose, et al. "An Effective AIDS Vaccine Based on Live Attenuated Vesicular Stomatitis Virus Recombinant", Cell, 2001; 106: 539-549.*
Irie, et al. "Modifications of the PSAP region of the matrix protein lead to attenuation of vesicular stomatitis virus in vitro and in vivo", J. Gen. Virol. 2007; 88(9): 2559-2567.*

(Continued)

*Primary Examiner* — Zachariah Lucas
*Assistant Examiner* — Stuart W Snyder
(74) *Attorney, Agent, or Firm* — Eduardo Krupnik

(57) ABSTRACT

Immunization platforms, immunization regimes and medicaments useful for inducing an immune response in a mammal and preventing or treating a pathogenic infection in a mammal, wherein said immunization platforms and medicaments comprise a recombinant vesicular stomatitis virus (VSV) of one serotype and a rVSV of another serotype and are used in a prime-boost immunization regime. In aspects of the invention one VSV serotype is Indiana and the other VSV serotype is New Jersey.

12 Claims, 21 Drawing Sheets

(56) References Cited

OTHER PUBLICATIONS

Rose, et al. An Effective AIDS Vaccine Based on Live Attenuated Vesicular Stomatitis Virus Recombinants. Cell, 2001; 106: 539-549.*
Kim and Kang Matrix protein of VSV New Jersey serotype containing methionine to arginine substitutions at positions 48 and 51 allows near-normal host cell gene expression. Virology, 2007; 357(1): 41-53.*
Wu, et al. Expression and processing of human immunodeficiency virus type 1 gp160 using the vesicular stomatitis virus New Jersey serotype vector system. J. Gen. Virol. 2009; 90(5): 1135-1140.*
Iyer, Arun V. et al, Recombinant Vesicular Stomatitis Virus-based West Nile Vaccine Elecits Strong Humoral and Cellular . . . , Vaccine, Feb. 2009, p. 893-903, vol. 27.
Rose, Nina F. et al, Glycoprotein Exchange Vectors Based on Vesicular Stomatitis Virus Allow Effective Boosting and Generation of . . . , J. of Virology, Dec. 2000, p. 10903-10910.
Wu, Kunyu et al, Expression and Processing of Human Immunodeficiency virus type 1 gp160 using the Vesicular Stomatitis Virus . . . , J. of Gen. Virology, 2009, p. 1135-1140, vol. 90.
Majid, Ayaz M. et al, Evaluating Replication-Defective Vesicular Stomatitis Virus as a Vaccine Vehicle, J. of Virology, Jul. 2006, p. 6993-7008, vol. 80 No. 14.
Kalinke, Ulrich et al, The Role of Somatic Mutation in the Generation of the Protective Humoral Immune Response against Vesicular . . . , Immunity, Dec. 1996, p. 639-652, vol. 5.
Johnson, Karl M. et al, Clinical and Serological Response to Laboratory-Acquired Human Infection by Indiana . . . , Amer. Jrnl of Tropical Medicine and Hygiene, 1996, p. 244-246, v15.
Gallione, Carol J. and Rose, John K., Nucleotide Sequence of a cDNA Clone Encoding . . . , J. of Virology, Apr. 1983, p. 162-169, vol. 46:1, American Society for Microbiology.
Fields, Bernard N. et al, Human Infection with the Virus Vesicular Stomatitis During an Epizootic, The New England J. of Medicine, Nov. 1967, p. 989-994, vol. 277:19.
Brandsma, Janet L. et al, Vesicular Stomatitis Virus-Based Therapeutic Vaccination Targeted to the E1, E2, E6 and E7 Proteins . . . , J. of Virology, Jun. 2007, p. 5749-5758, v81:11.
Carwright, B. and Brown, F., Serological Relationships between Different Strains of Vesicular Stomatis Virus, J. gen. Virol., May 1972, p. 391-398, vol. 16.

Clarke, David K., Recombinant Vesicular Stomatitis Virus as an HIV-1 Vaccine Vector, Springer Semin Immun, Jun. 2006, p. 239-253, vol. 28, Springer-Verlag.
Daddario-Dicaprio, Kathleen et al, Cross-Protection against Marburg Virus Strains by Using a Live, Attenuated Recombinant Vaccine, J. of Virology, Oct. 2006, p. 9659-9666, v80.
Lawson, Nathan D. et al, Recombinant Vesicular Stomatitis Viruses from DNA, Proc Natl Acad Sci, May 1995, p. 4477-4481, vol. 92 No. 10, JSTOR.
Kim, Gyoung Nyoun and Kang, C. Yong, Matrix Protein of VSV New Jersey Serotype Containing Methionine to Arginine Substitutions at Positions . . . , Virology, 2007, p. 41-53, v357.
Kohl, Wiebke et al, Expression of Surface Glycoprotein E2 of Bovine Viral Diarrhea Virus by Recombinant Vesicular Stomatitis Virus, J. of Gen Virology, 2007, p. 157-165, vol. 88.
Kuate, Seraphin et al, Exosomal Vaccines Containing the S Protein of the SARS Coronavirus Induce High Levels of Neutralizing Antibodies, Virology, 2007, p. 26-37, vol. 362.
Petersen, Jeannine M. et al, The Matrix Protein of Vesicular Stomatitis Virus Inhibits Nucleocytoplasmic Transport . . . , Mole and Cell Bio, Nov. 2000, p. 8590-8601, vol. 20 No. 22.
Palin, Amy et al, An Optimized Vaccine Vector based on Recombinant Vesicular Stomatitis Viruse Gives . . . , Vaccine, 2007, p. 741-750, vol. 25, Elsevier Ltd.
Yewdell, Jonathan W. et al, Recognition of Cloned Vesicular Stomatitis Virus Internal and External Gene Products . . . , J. of Experimnetal Med., Jun. 1986, p. 1529-1538, vol. 163.
Schwartz, Jennifer A. et al, Vesicular Stomatitis Virus Vecotrs Expressing Avian Influenza H5 HA Induce . . . , Virology, 2007, p. 166-173, vol. 366, Elsevier Inc.
Von Kobbe, Cayetano et al, Vesicular Stomatitis Virus Matrix Protein Inhibits Host Cell Gene Expression by Targeting the Nucleoporin Nup98, Molecular Cell, 2000, p. 1243-1252.
Whelan, Sean et al, Efficient Recovery of Infectious Vesicular Stomatitis Virus Entirely from cDNA Clones, Proc. Natl. Acad. Sci., Aug. 1995, p. 8388-8392, vol. 92 No. 18, JSTOR.
Puddington, Lynn et al, N Protein is the Predominant Antigen Recognized by Vesicular Stomatitis Virus-Specific Cytotoxic T Cells, J. of Virology, Nov. 1986, p. 704-717, v60:2.
Rose, Nina F. et al, An Effective AIDS Vaccine Based on Live Attenuated Vesicular Stomatitis Virus Recombinants, Cell, Sep. 2001, p. 539-549, vol. 106, Cell Press.

* cited by examiner

DIFFERENT SEROTYPES OF VESICULAR STOMATITIS VIRUS AS EXPRESSION VECTORS FOR IMMUNIZATION REGIMENS

CROSS REFERENCE TO RELATED APPLICATIONS

This application is a national stage application under 35 U.S.C. 371 of International Application No. PCT/CA2010/000874, filed Jun. 8, 2010, which in turn claims the benefit under 35 U.S.C. 119(e) of U.S. Provisional Ser. No. 61/184,959, filed Jun. 8, 2009, the contents of each of which are hereby incorporated by reference into the present disclosure.

FIELD OF THE INVENTION

The present invention relates to a novel platform of vaccines or immunogenic compositions comprising two different serotypes of recombinant vesicular stomatitis viruses and to the use of the novel platform in compositions and methods for prophylactic and therapeutic vaccination regimens against human pathogens.

BACKGROUND OF THE INVENTION

Throughout this application, various references are cited in square brackets to describe more fully the state of the art to which this invention pertains. The disclosure of these references is hereby incorporated by reference into the present disclosure.

The best way to prime CD8+ CTL is to synthesize the target antigens by DNA transfection or infection using viral or bacterial vectors. The requirements as viral vaccine vectors are a broad range of hosts and good expression of gene of interests. Vesicular stomatitis virus (VSV) infects most mammalian cells and expresses viral proteins up to 60% of total proteins in infected cells [Kim, G. N., and C. Y. Kang. Virology 357: 41, 2007]. In nature VSV infects pigs, cattle, and horses, and causes vesicular disease around the mouth and foot. Although human infection by VSV has been reported, VSV does not cause any serious symptoms [Fields, B. N., and K. Hawkins. N Engl J Med 277:989, 1967; Johnson, K. M. et al. Am J Trop Med Hyg 15:244, 1966].

VSV is a negative stranded RNA virus which encodes five proteins, nucleocapsid protein (N), phosphoprotein (P), matrix protein (M), surface glycoprotein (G), and RNA dependent RNA polymerase (L). The N, P, and L proteins of VSV are required for synthesis of positive sense and negative sense genomic RNAs and mRNA, which are necessary for the synthesis of VSV proteins, as well as gene of interest such as Human Hepatitis C virus (HCV) proteins.

Since the development of VSV reverse genetics system [Lawson, N. D., et al. Proc Natl Acad Sci USA 92:4477, 1995; Whelan, S. P. et al. Proc Natl Acad Sci USA 92:8388, 1995] to generate recombinant VSVs from cDNA, VSV has been studied as a viral vaccine vector for the immunization of various pathogens [Brandsma, J. L., et al. J Virol 81:5749, 2007; Daddario-DiCaprio, K. M., et al. J Virol 80:9659, 2006; Kohl, W., et al. J Gen Virol 88:157, 2007; Kuate, S., et al. Virology 362:26, 2007; Palin, A., et al. Vaccine 25:741, 2007; Schwartz, J. A., et al. Virology 366:166, 2007].

Although VSV is a rapidly replicating virus, eventually humoral and cellular immune responses against VSV will be elicited in the animal host, like any other viral vectors [Yewdell, J. W. et al. J Exp Med 163:1529-1938, 1986; Puddington, L. et al. J Virol 60:708-717, 1986; Kalinke, U. et al Immunity 5:639-652, 1996]. Animals infected with VSV develop immune responses in one or two weeks including a neutralizing antibody [Kalinke, U. et al Immunity 5:639-652, 1996], which hinders the efficacy of boost immunizations for vaccination with the same vector. VSV is neutralized by serotype specific antibodies against viral surface glycoprotein G. Two different serotypes of VSV, VSV-Indiana ($VSV_{Ind}$) and VSV-New Jersey ($VSV_{NJ}$) show 50% amino acid identity in the glycoprotein [Gallione, C. J., and Rose, J. K. J. Virol. 46:162-169, 1983]. Antibodies raised against one serotype of VSV do not neutralize the other serotype of VSV [Cartwright, B., and Brown, F. J. Gen. Virol. 16:391-398, 1972]. Therefore, others have used $VSV_{Ind}$ as a vaccine vector in which the glycoprotein was replaced with that of $VSV_{NJ}$ to minimize the problems arising from this immune response against the viral vectors [Rose, N. F. et al. J. Virol. 74:10903-10910, 2000; Rose, N. F. et al. Cell 106:539-549, 2001].

Although the $VSV_{Ind}$ with G protein of $VSV_{NJ}$ serotype is useful in evading the humoral immune response, it will not prevent the cellular immune response which can be triggered by other VSV proteins including N, P, M, and L proteins. The cellular immune responses against VSV proteins other than the G protein may result in incomplete immune responses against the antigen of interest. Therefore, generation of additional recombinant VSV from another serotype can increase the efficacy of using VSV as a live viral vaccine vector.

Interestingly, it has been previously suggested that generation of a complete $rVSV_{NJ}$ serotype vector was not attempted due to the potential for cross-reactive cytotoxic T-lymphocyte responses between the Indiana and New Jersey serotypes [Clarke et al., Springer Semin Immun 28:239, 2006].

In view of the above background, it would be advantageous to provide an approach for immunoprophylaxis and immunotherapy utilizing both humoral and cellular immune systems. As such, the Applicant has developed a system comprising a combination of vaccines that elicits a response against infectious agents.

SUMMARY OF THE INVENTION

In one aspect the present invention provides for an immunization platform for use in a prime boost immunization strategy characterized in that said immunization platform comprises: (a) one vaccine or immunogenic composition comprising a recombinant vesicular stomatitis virus (rVSV) of one serotype, and (b) another vaccine or immunogenic composition comprising a rVSV of another serotype.

In one aspect of the present invention the immunization platform is characterized in that one serotype is Indiana and the other serotype is New Jersey.

In another aspect of the present invention the immunization platform is characterized in that each one of the two rVSV serotypes include a mutant matrix protein (M) gene.

In another aspect of the present invention the immunization platform is characterized in that one serotype includes a surface glycoprotein (G) gene of the other serotype.

In another aspect of the present invention the immunization platform is characterized in that the two rVSV serotypes are capable of expressing one or more proteins of interest.

In another aspect of the present invention the immunization platform is characterized in that the two rVSV serotypes are capable of expressing one or more Hepatitis C virus (HCV) proteins.

In a further aspect the present invention provides for an immunization regimen characterized in that said immunization regimen comprises administering to a subject a prime dose of a vaccine or immunogenic composition comprising a rVSV of a first serotype followed by a boost dose of a vaccine or immunogenic composition comprising a rVSV of second serotype.

In one aspect, the immunization regimen is characterized in that the boost dose is followed by at least one more dose of the vaccine or immunogenic composition comprising the rVSV of the first serotype.

In another aspect the immunization regimen is characterized in that first serotype is Indiana and the second serotype is New Jersey.

In another aspect the immunization regimen is characterized in that first serotype is New Jersey and the second serotype is Indiana.

In another aspect the immunization regimen is characterized in that the first and the second rVSV serotypes include a mutant M gene.

In another aspect the immunization regimen is characterized in that the second rVSV serotype includes the G gene of the first rVSV serotype.

In another aspect the immunization regimen is characterized in that the first and second rVSV serotypes are capable of expressing one or more proteins of interest.

In another aspect the immunization regimen is characterized in that said one or more proteins of interest are one or more proteins of an exogenous virus selected from the group comprising of: HCV, Human Immunodeficiency Virus (HIV), West Nile virus, Hantaviruses, Influenza virus, Ebola virus, Dengue hemorrhagic fever virus, Japanese encephalitis virus, SARS Coronavirus.

In another aspect the immunization regimen is characterized in that the first and second rVSV serotypes are capable of expressing one or more HCV proteins.

In another aspect the immunization regimen is characterized in that the first serotype is Indiana and the second serotype is New Jersey, wherein both the rVSV Indiana and the rVSV New Jersey include a mutant M gene, and wherein the rVSV Indiana and the rVSV New Jersey are capable of expressing one or more proteins of an exogenous virus.

In a further aspect yet, the present invention provides for a method for inducing an immune response in a mammal to a VSV characterized in that said method comprises the following steps: (a) administering to the mammal an effective amount of a first vaccine or immunogenic composition, wherein said first vaccine or immunogenic composition comprises a rVSV of a first serotype, and (b) administering to the subject an effective amount of a second vaccine or immunogenic composition, wherein said second vaccine or immunogenic composition comprises a rVSV of a second serotype.

In one aspect the method of the present invention for inducing an immune response in a mammal to a VSV is characterized in that said method further comprises: (c) administering to the subject an effective amount of the first vaccine or immunogenic composition.

In another aspect the method of the present invention for inducing an immune response in a mammal to a VSV is characterized in that the first serotype is Indiana and the second serotype is New Jersey.

In another aspect the method of the present invention for inducing an immune response in a mammal to a VSV is characterized in that the first serotype is New Jersey and the second serotype is Indiana.

In another aspect the method of the present invention for inducing an immune response in a mammal to a VSV is characterized in that the first and the second rVSV serotypes include a mutant M gene.

In another aspect the method of the present invention for inducing an immune response in a mammal to a VSV is characterized in that the second rVSV serotype includes the G gene of the first rVSV serotype.

In another aspect the method of the present invention for inducing an immune response in a mammal to a VSV is characterized in that characterized in that the immune response includes a humoral and/or a cellular immune response.

In another aspect the method of the present invention for inducing an immune response in a mammal to a VSV is characterized in that the first and second rVSV serotypes are capable of producing virus-like particles having the ability to elicit a cell-mediated and/or humoral immune response.

In another aspect the method of the present invention for inducing an immune response in a mammal to a VSV is characterized in that the first and the second rVSV serotypes are capable of expressing one or more proteins of an exogenous virus, and said immune response further comprises an immune response to the one or more exogenous virus proteins, wherein said exogenous virus is selected from the group comprising of Human HCV, HIV, West Nile virus, Hantaviruses, Influenza virus, Ebola virus, Dengue hemorrhagic fever virus, Japanese encephalitis virus, SARS Coronavirus.

In another aspect the method of the present invention for inducing an immune response in a mammal to a VSV is characterized in that the first and second rVSV serotypes are capable of expressing one or more HCV proteins, and said immune response further comprises an immune response to the one or more HCV proteins.

In yet a further aspect the present invention provides for a combined medicament useful for inducing an immune response against a pathogen, characterized in that said combined medicament comprises: (a) one vaccine or immunogenic composition comprising a rVSV of one serotype that is capable of expressing one or more proteins of the pathogen, and (b) another vaccine or immunogenic composition comprising a rVSV of another serotype that is capable of expressing the one or more proteins of the pathogen.

In one aspect the combined medicament is characterized in that one serotype is a rVSV Indiana and the other serotype is a rVSV New Jersey, wherein the rVSV Indiana and rVSV New Jersey include a mutant M gene.

In a further aspect of the present invention a method is provided for preventing or treating an infection caused by a pathogen, characterized in that said method comprises: (a) administering to a subject an effective amount of a first vaccine or immunogenic composition comprising a rVSV of a first serotype that is capable of expressing one or more proteins of the pathogen, and (b) administering to the subject an effective amount of a second vaccine or immunogenic composition comprising a rVSV of a second serotype that is capable of expressing the one or more proteins of the pathogen.

In one aspect the method of the present invention for preventing or treating an infection caused by a pathogen is characterized in that said method further comprises: (c) administering to the subject an effective amount of the first vaccine or immunogenic composition.

In another aspect the method of the present invention for preventing or treating an infection caused by a pathogen is characterized in that the first serotype is a rVSV Indiana and the second serotype is a rVSV New Jersey.

In another aspect the method of the present invention for preventing or treating an infection caused by a pathogen is characterized in that the first serotype is a rVSV New Jersey and the second serotype is a rVSV Indiana.

In a further aspect yet the present invention provides for a kit comprising: (a) at least one dose of an effective amount of a vaccine comprising a rVSV of one serotype, and (b) at least one dose of an effective amount of a vaccine comprising a rVSV of another serotype.

In one aspect the kit of the present invention is characterized in that (a) and (b) are formulated in a pharmaceutically acceptable carrier.

Advantages of using VSV and two serotypes of VSV as a vaccine vectors include:

(1) Utilization of two serotypes of VSV makes the VSV a more effective vaccine vector, because one serotype of VSV (first vaccine) will not neutralize the other serotype of VSV (second vaccine) or easily kill the cells infected with the other serotype of VSV.

(2) VSV does not cause serious disease in humans and most people infected are veterinarians dealing with the sick animals or scientists working with the VSV. Therefore, the seropositive rate in a general human population is very low, which makes the VSV an attractive vaccine vector.

(3) VSV replicates in a self-limiting manner in an infected individual, but it still induces strong cellular and humoral immune responses.

(4) VSV replicates well in most of the mammalian cells in culture and yields high viral titer.

BRIEF DESCRIPTION OF THE DRAWINGS

The present invention will become more fully understood from the detailed description given herein and from the accompanying drawings, which are given by way of illustration only and do not limit the intended scope of the invention.

Figure 6:
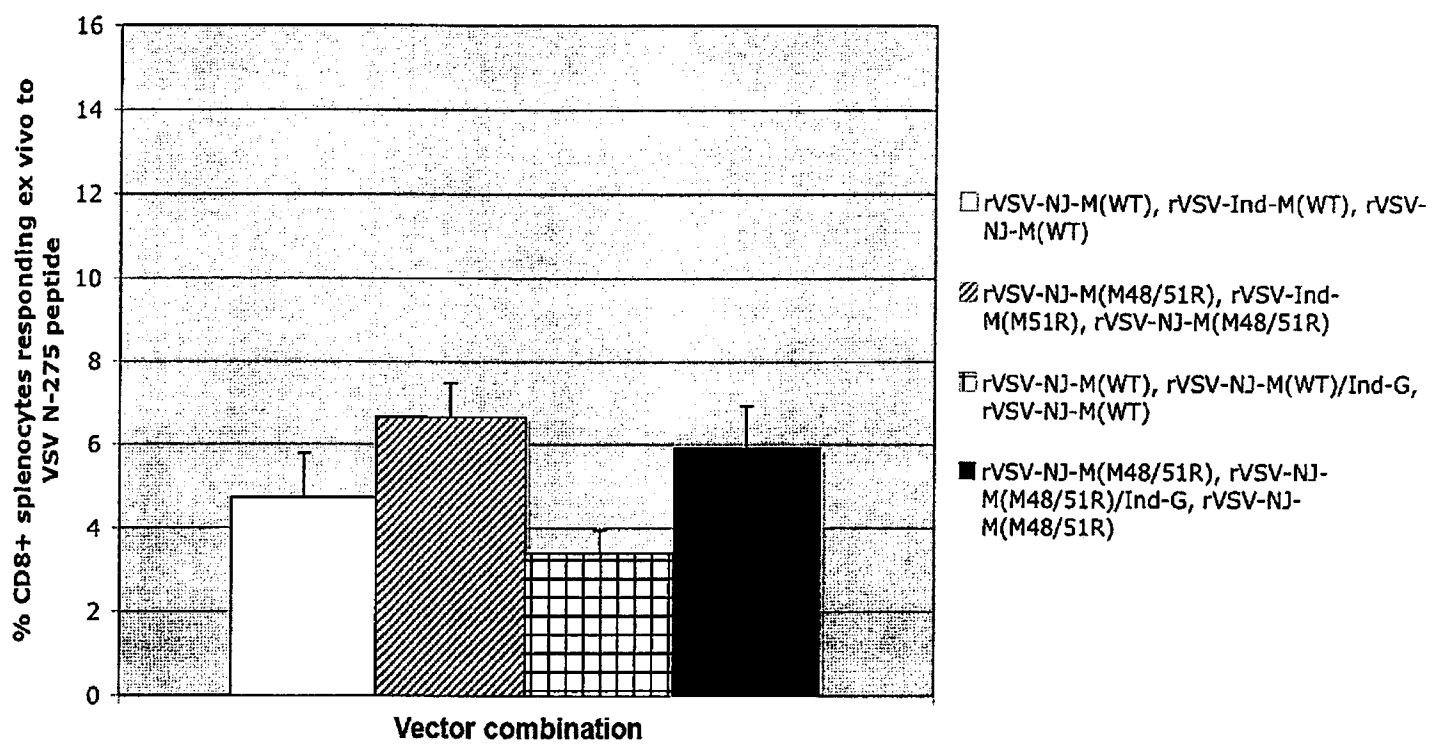

FIG. 6 depicts VSV peptide specific CD8+ T cell responses in Balb/c mice receiving in a successive dosing schedule of VSV vaccines in the order of New Jersey-Indiana-New Jersey.

Figure 7:
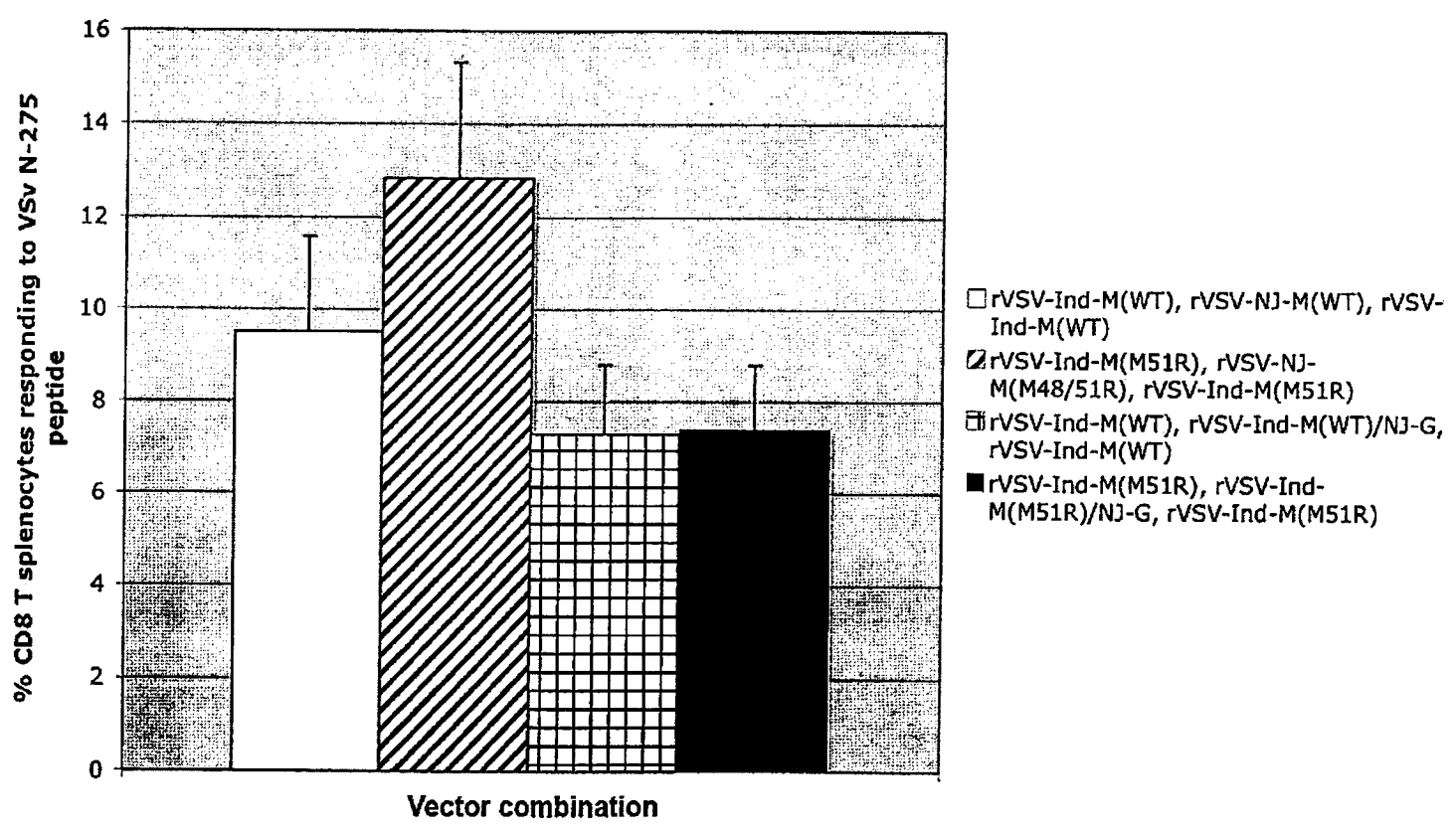

FIG. 7 depicts VSV peptide specific CD8+ T cell responses in Balb/c mice receiving in a successive dosing schedule of VSV vaccines in the order of Indiana-New Jersey-Indiana.

FIG. 8 B depicts the comparison of re-activation of CD8+ T cells following ex vivo stimulation with HCV MHC class I peptides in a cohort of mice (n=2) vaccinated with $VSV_{Ind}$-M(M51R)+HCV-CoreΔER, then $VSV_{NJ}$-M(M48/51R)+HCV-CoreΔER, followed 3 weeks later by an additional dose of $VSV_{Ind}$-M(M51R)+HCV-CoreΔER (set of bars on right of panel).

Figure 11:
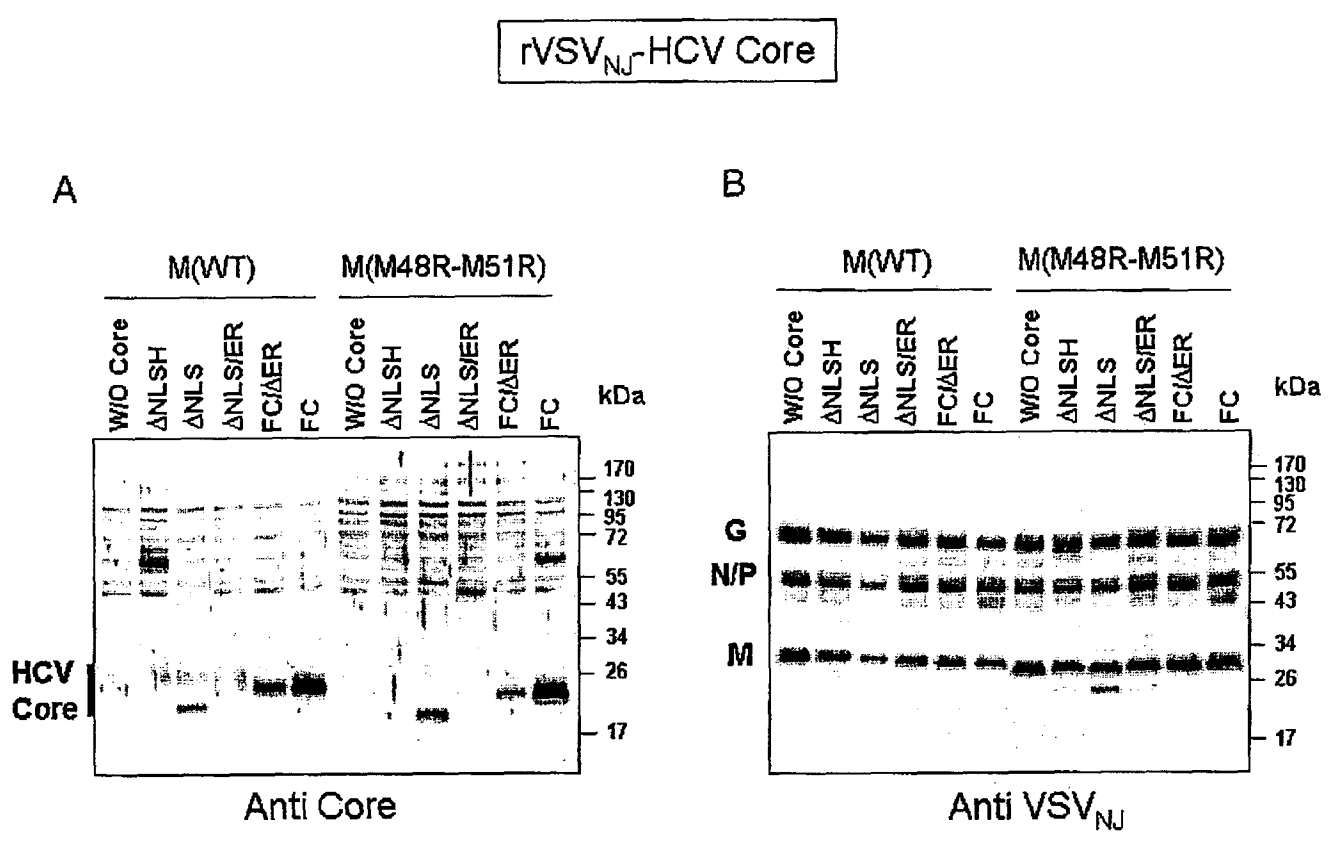

FIG. 11 depicts the expression of HCV Core proteins from the recombinant $VSV_{NJ}$ M wild type and M mutant (A). The expression of the VSV proteins from the same cells was detected as well (B). The expression was determined by Western blot analysis using Core antibody or $VSV_{NJ}$ antibody.

Figure 12:
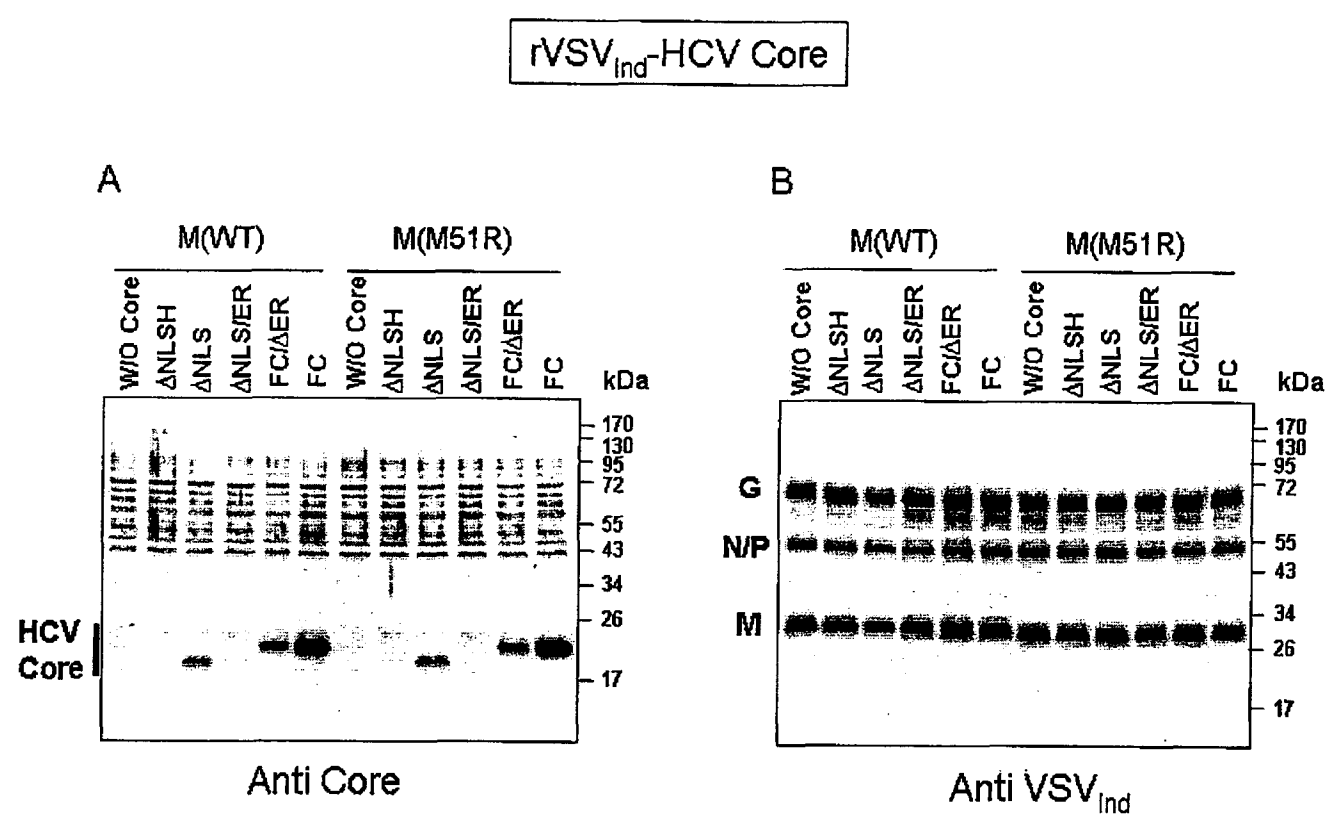

FIG. 12 depicts the expression of HCV Core proteins from the recombinant $VSV_{Ind}$ M wild type and M mutant (A). The expression of the VSV proteins from the same cells was detected as well (B). The expression was determined by Western blot analysis using Core antibody or $VSV_{NJ}$ antibody.

Figure 16:
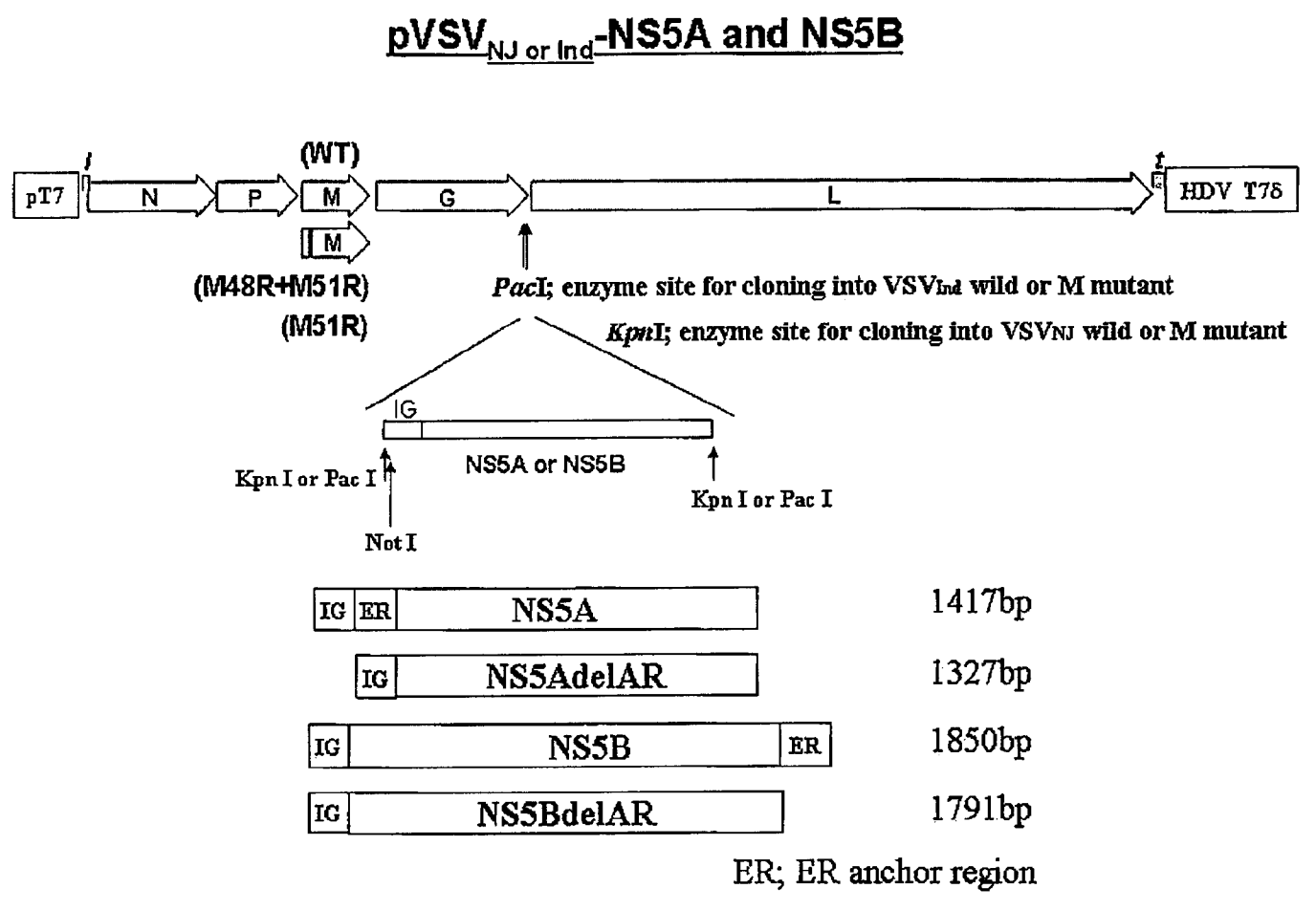

FIG. 16 illustrates the cloning of HCV NS5A and NS5B genes into the cDNA clone of $rVSV_{NJ}(M_{WT})$, $rVSV_{NJ}(M_{M48R-M51R})$, $rVSV_{Ind}(M_{WT})$, and $rVSV_{Ind}(M_{M51R})$.

Figure 17:
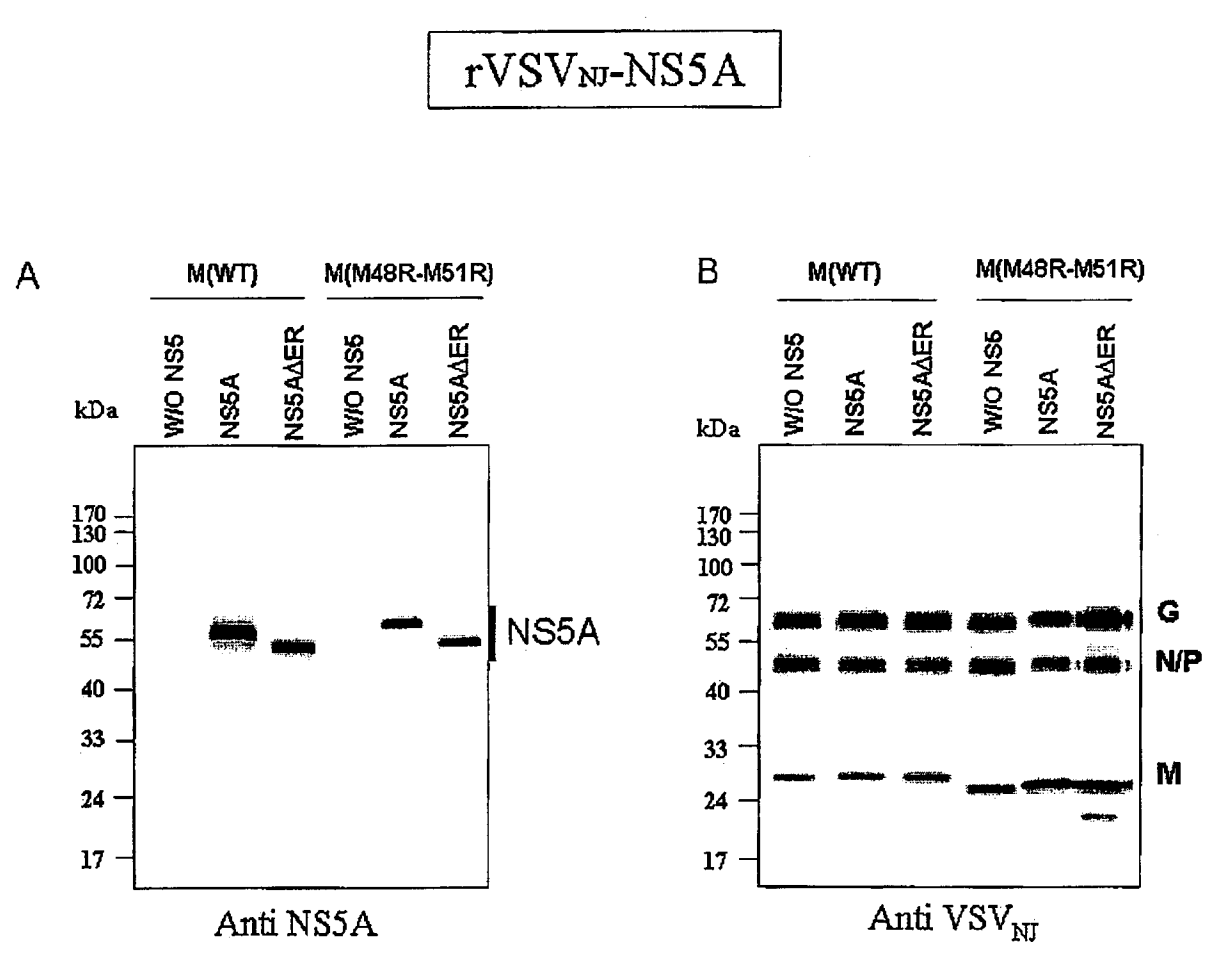

FIG. 17 depicts the recovered $rVSV_{NJ}(M_{WT})$, $rVSV_{NJ}(M_{M48R-M51R})$ expressing NS5A. Expression of NS5A, serotypes and M phenotypes of the recovered rVSV was confirmed by Western blot analysis using the HCV NS5A antibody and serotype specific $VSV_{NJ}$ antibodies.

Figure 18:
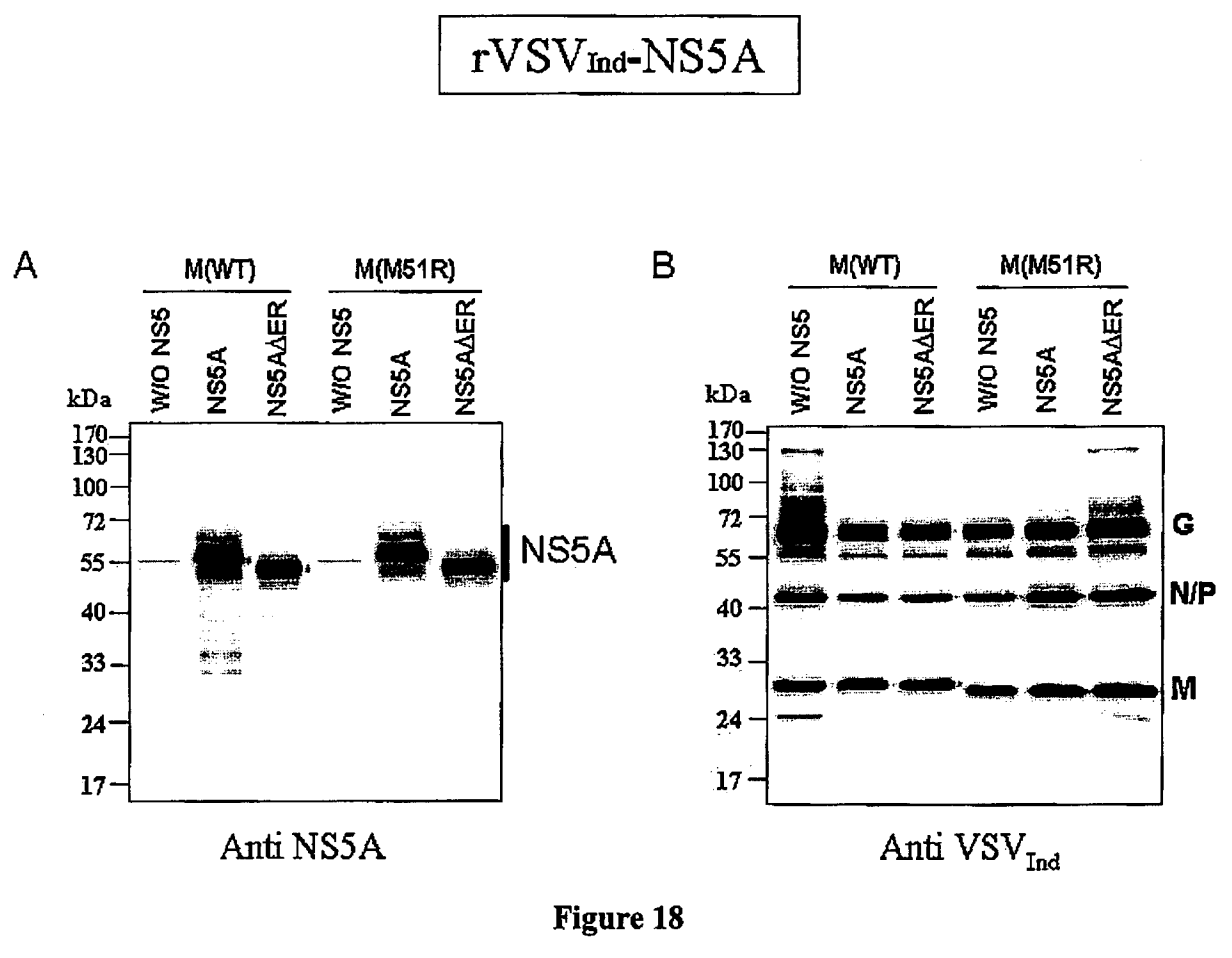

FIG. 18 depicts the recovered $rVSV_{Ind}(M_{WT})$, and $rVSV_{Ind}(M_{M51R})$ expressing NS5A. Expression of NS5A, serotypes and M phenotypes of the recovered rVSV was confirmed by Western blot analysis using the HCV NS5A antibody and serotype specific $VSV_{Ind}$ antibodies.

Figure 19:
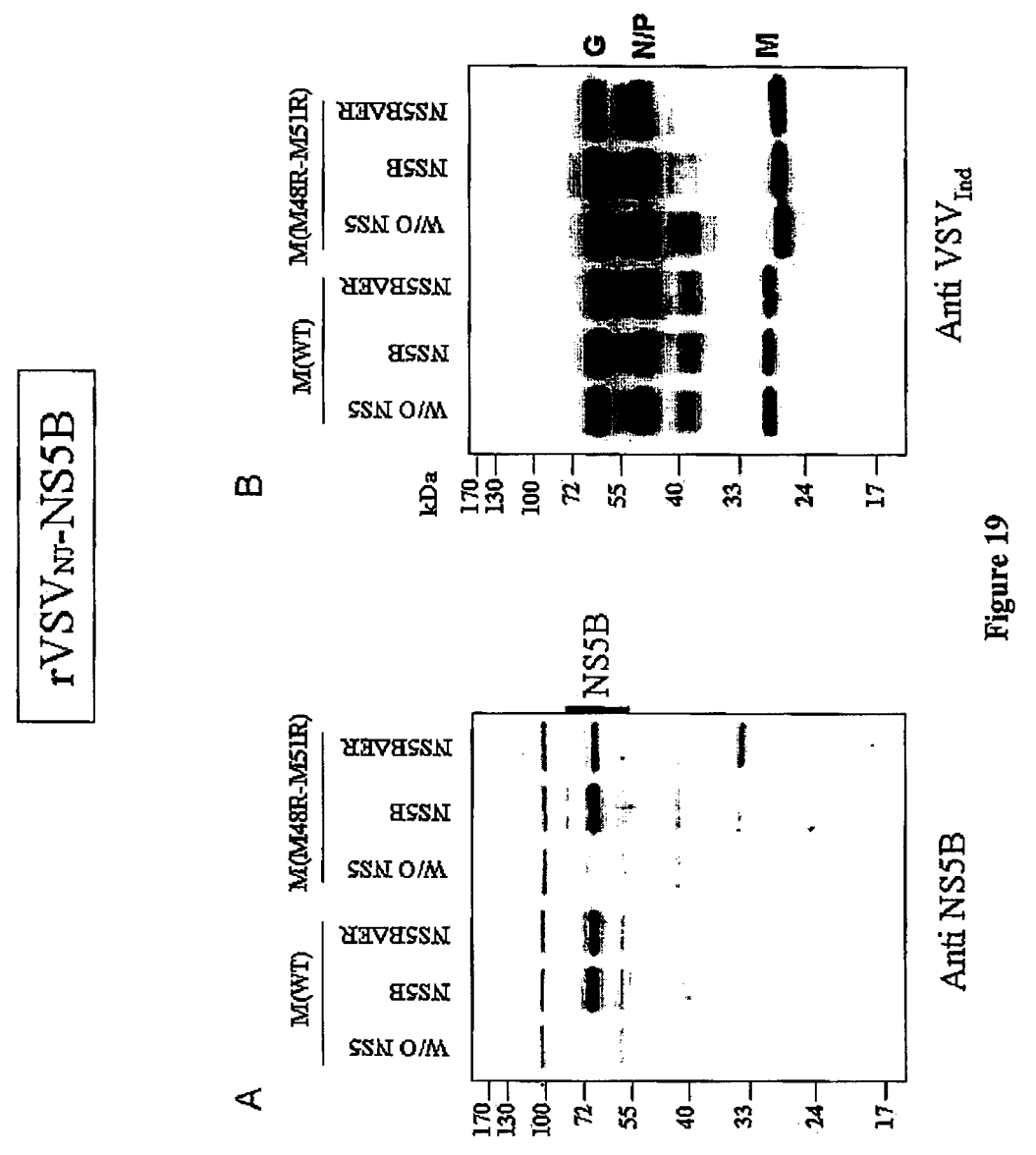

FIG. 19 depicts the recovered $rVSV_{NJ}(M_{WT})$, $rVSV_{NJ}(M_{M48R-M51R})$, expressing NS5B. Expression of NS5B, serotypes and M phenotypes of the recovered rVSV was confirmed by Western blot analysis using the HCV NS5B antibody and serotype specific $VSV_{NJ}$ antibodies.

DETAILED DESCRIPTION OF THE INVENTION

1. Definitions

Figure 1:
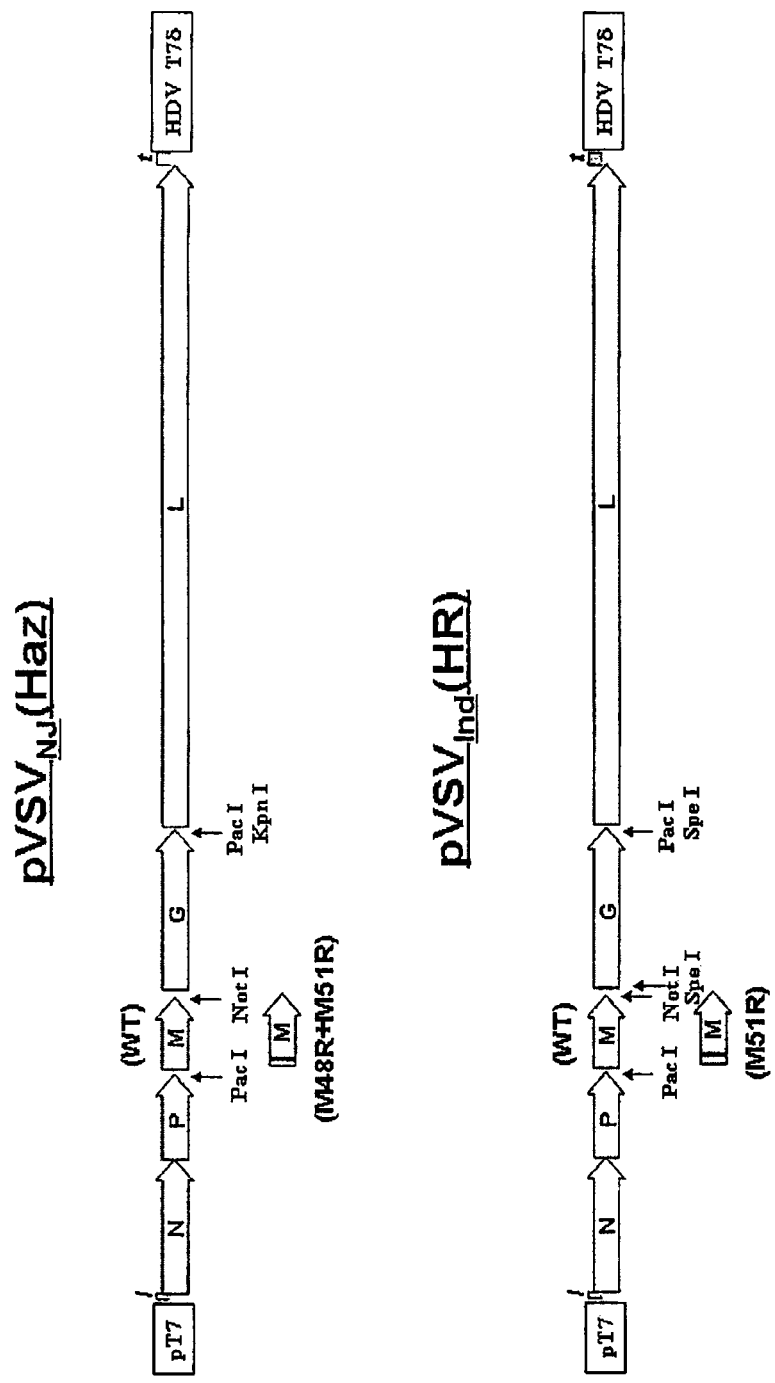
FIG. 1 illustrates gene organization of vesicular stomatitis virus (VSV), Indiana (Ind) serotype Heat resistant (HR) strain and New Jersey (NJ) serotype Hazlehurst strain (Haz).

For convenience, the meaning of certain terms and phrases employed in the specification, examples, and appended claims are provided below. Unless defined otherwise, all technical and scientific terms used herein have the same meaning as commonly understood by one of ordinary skill in the art to which this invention belongs.

The articles "a" and "an" are used herein to refer to one or more than one (i.e., to at least one) of the grammatical object of the article.

The terms "animal" and "subject" as used herein includes all members of the animal kingdom including mammals, preferably humans.

The term "effective amount" as used herein means an amount effective and at dosages and for periods of time necessary to achieve the desired result.

The term "Indiana", and "IND" are used to refer to the VSV serotype Indiana ($VSV_{Ind}$).

"$M_{WT}$" "M(WT)" are used to refer to VSV having a wild type M gene. "M51R" is used to refer to an M gene in the $VSV_{Ind}$ having a methionine changed to an arginine at position 51. M48R-M51R" is used to refer to an M gene in $VSV_{NJ}$ having a methionine changed to an arginine at positions 48 and 51.

The term "New Jersey", and "NJ" are used to refer to the VSV serotype New Jersey ($VSV_{NJ}$).

"Ind-M(M51R)/NJ G" is used to refer to $VSV_{Ind}$ having a mutant M gene and expressing VSV serotype New Jersey ($VSV_{NJ}$) G protein. "Ind-M(WT)/NJ G" is used to refer to $VSV_{Ind}$ having a wild type M protein and expressing a $VSV_{NJ}$ G protein.

"NJ-M (M48R-M51R)/Ind G" is used to refer to $VSV_{NJ}$ having a mutant M gene and expressing a $VSV_{Ind}$ G protein. "NJ-M(WT)/Ind G" is used to refer to $VSV_{NJ}$ having a wild type M gene and expressing a $VSV_{Ind}$ G protein.

The term "protein" as used herein is defined as a chain of amino acid residues, usually having a defined sequence. As used herein the term protein is inclusive of the terms "peptides" and "proteins". The terms also encompass an amino acid polymer that has been modified.

"rVSV" is used to refer to a recombinant vesicular stomatitis virus.

2. Overview

The present invention features immunization platforms, immunization regimens and medicaments useful for inducing an immune response in a subject and preventing or treating a pathogenic infection in a subject, wherein said platforms, regimens and medicaments comprise a recombinant VSV of one serotype, and a recombinant VSV of another serotype. Prior to the present invention, other research groups used the surface glycoprotein (G) gene switched VSVs for the second immunization to prevent the neutralization of the booster virus by the antibodies elicited by the prime viruses. Prior to the present invention, however, no other research groups have used two different serotypes of rVSV in a prime and boost immunization scheme or strategy.

Thus, in one aspect, the present invention provides for an immunization platform for use in a prime boost immunization strategy characterized in that said immunization platform comprises:
(a) one vaccine or immunogenic composition comprising a recombinant vesicular stomatitis virus (rVSV) of a one serotype, and
(b) another vaccine or immunogenic composition comprising a rVSV of another serotype.

In another aspect, the present invention provides for a combined medicament useful for inducing an immune response against a pathogen, characterized in that said combined medicament comprises:
(a) one vaccine or immunogenic composition comprising a rVSV of one serotype that is capable of expressing one or more proteins of the pathogen, and
(b) another vaccine or immunogenic composition comprising a rVSV of another serotype that is capable of expressing the one or more proteins of the pathogen.

Figure 2:
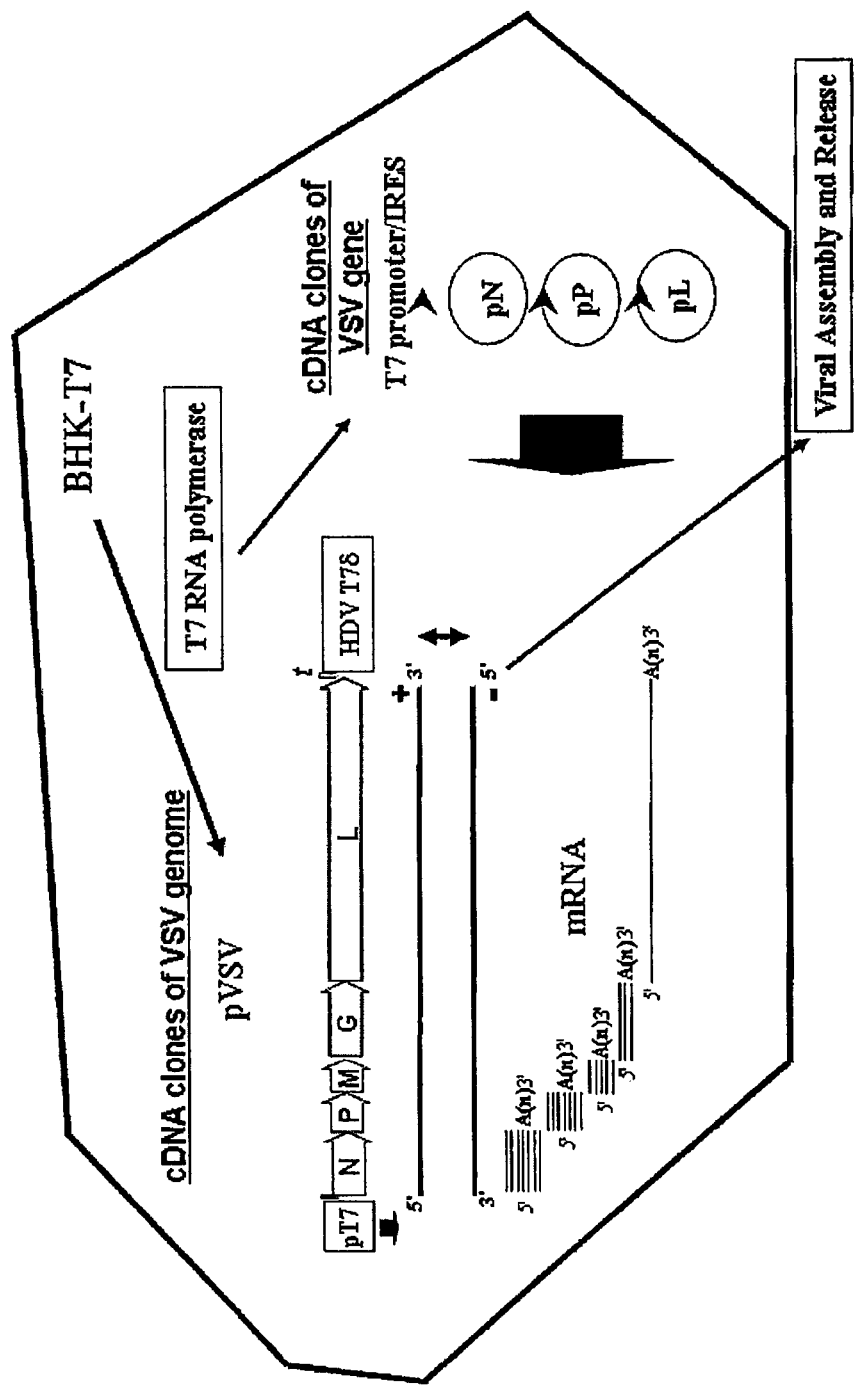
FIG. 2 illustrates a reverse genetics system for the recovery of VSV from cDNA.

The Applicant developed a reverse genetics system to recover $VSV_{NJ}$ from cDNA for the first time [see FIGS. 1 and 2; Kim, G. N. and Kang, C. Y., Virology, 357:41-53, 2007]. The recombinant $VSV_{NJ}$ is an effective viral vector together with $VSV_{Ind}$ for the expression of foreign genes (i.e. genes of exogenous viruses), which can be used to minimize problems associated with preexisting immune responses against VSV itself. In addition to the $VSV_{NJ}$ vector system, the Applicant also generated a full length clone of $VSV_{Ind}$ (FIG. 1) that can used as an expression vector to avoid neutralization of VSV vectors after the boost immunization.

The characteristics of Applicant's rVSV immunization platform include, in one aspect, the usage of two different serotypes of VSV, and, in another aspect, the usage of VSVs with wild type M gene and mutant M gene. In aspects of the invention the two different VSV serotypes are $VSV_{Ind}$ and $VSV_{NJ}$.

VSV M protein inhibits cellular protein synthesis very efficiently, but when a methionine is changed to arginine at position 51 in the $VSV_{Ind}$ M and at positions 48 and 51 in the $VSV_{NJ}$ M, M proteins lose their inhibitory effect on the host cellular protein expression [Kim, G. N., and C. Y. Kang. Virology 357:41, 2007; Petersen, J. M., et al. Mol Cell Biol 20:8590, 2000; von Kobbe, C., et al. Mol Cell 6:1243, 2000]. The rVSV with the mutant M gene can, therefore, be a better expression vectors than rVSV with wild type M, because they will not block the expression of immune related proteins such as chemokines in the antigen presenting cells.

3. Vaccines or Immunogenic Compositions of the Invention

The present invention further features vaccines or immunogenic compositions comprising an rVSV of a first serotype and vaccines or immunogenic compositions comprising an rVSV of a second serotype, as described above. The vaccine or immunogenic compositions of the invention are suitable for administration to subjects in a biologically compatible form in vivo. The expression "biologically compatible form suitable for administration in vivo" as used herein means a form of the substance to be administered in which any toxic effects are outweighed by the therapeutic effects. The substances may be administered to any animal or subject, preferably humans. The vaccines of the present invention may be provided as a lyophilized preparation. The vaccines of the present invention may also be provided as a solution that can be frozen for transportation. Additionally, the vaccines may contain suitable preservatives such as glycerol or may be formulated without preservatives. If appropriate (i.e. no damage to the VSV in the vaccine), the vaccines may also contain suitable diluents, adjuvants and/or carriers.

The dose of the vaccine may vary according to factors such as the disease state, age, sex, and weight of the individual, and the ability of antibody to elicit a desired response in the individual. Dosage regime may be adjusted to provide the optimum therapeutic response. The dose of the vaccine may also be varied to provide optimum preventative dose response depending upon the circumstances.

4. Methods of Use

The present invention also features methods of inducing an immune response in a subject and preventing or treating a pathogenic infection in a subject comprising administering to the subject an effective amount of a combination of vaccines or immunogenic compositions.

As such, in one aspect, the present invention provides for a method for inducing an immune response in a mammal to a VSV characterized in that said method comprises the following steps:
(a) administering to the mammal an effective amount of a first vaccine or immunogenic composition, wherein said first vaccine or immunogenic composition comprises a rVSV of a first serotype, and (b) administering to the subject an effective amount of a second vaccine or immunogenic composition, wherein said second vaccine or immunogenic composition comprises a rVSV of a second serotype.

In another aspect, the present invention also provides for a method for preventing or treating an infection caused by a pathogen, characterized in that said method comprises: (a) administering to a subject an effective amount of a first vaccine or immunogenic composition comprising a rVSV of a first serotype that is capable of expressing one or more proteins of the pathogen, and (b) administering to the subject an effective amount of a second vaccine or immunogenic composition comprising a rVSV of a second serotype that is capable of expressing the one or more proteins of the pathogen.

In aspects of the invention the methods for inducing an immune response in a mammal to a VSV and the methods for preventing or treating an infection caused by a pathogen may further comprise step (c) administering to the subject an effective amount of the first vaccine or immunogenic composition. Step (c) may be administered to the subject more than one time over the course of inducing an immune response, preventing or treating.

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitation.

EXAMPLES

The examples are described for the purposes of illustration and are not intended to limit the scope of the invention.

Example 1

Recovery of VSV by Reverse Genetics

The Applicant generated recombinant VSVs from cDNA by reverse genetics system, which was established before by Rose and Wertz, separately [Lawson, N. D., et al. Proc Natl Acad. Sci USA 92:4477, 1995; Whelan, S. P. et al. Proc Nati Acad Sci USA 92:8388, 1995]. Baby hamster kidney cells expressing bacteriophage T7 RNA polymerase, namely BHK-T7 cells [Buchholz, U. J. et al. J Virol 73:251, 1999], were transfected with a DNA plasmid encoding full length genome of VSV, Indiana serotype or New Jersey serotype, and plasmids encoding VSV N, P, and L genes. Cell culture medium containing newly generated virus was harvested 48-72 hours after transfection depending on the degree of cytopathic effects by the recombinant VSV. FIG. 2 illustrates the reverse genetics system for the recovery of VSV from cDNA.

FIG. 1 illustrates the cDNA clones of $VSV_{Ind}$ and $VSV_{NJ}$ generated by the Applicant. The diagram of FIG. 1 describes the gene order (N, P, M, G, and L) and restriction enzyme sites (Pac I, Not I, Kpn I, and Spe I) in the full-length DNA clone of VSV genome, which can be used to clone gene of interests (foreign genes) into the VSV genome. The mutations introduced into the M gene (M51R in the $VSV_{Ind}$ and M48R-M51R in the $VSV_{NJ}$) of VSV are shown as well.

Figure 3:
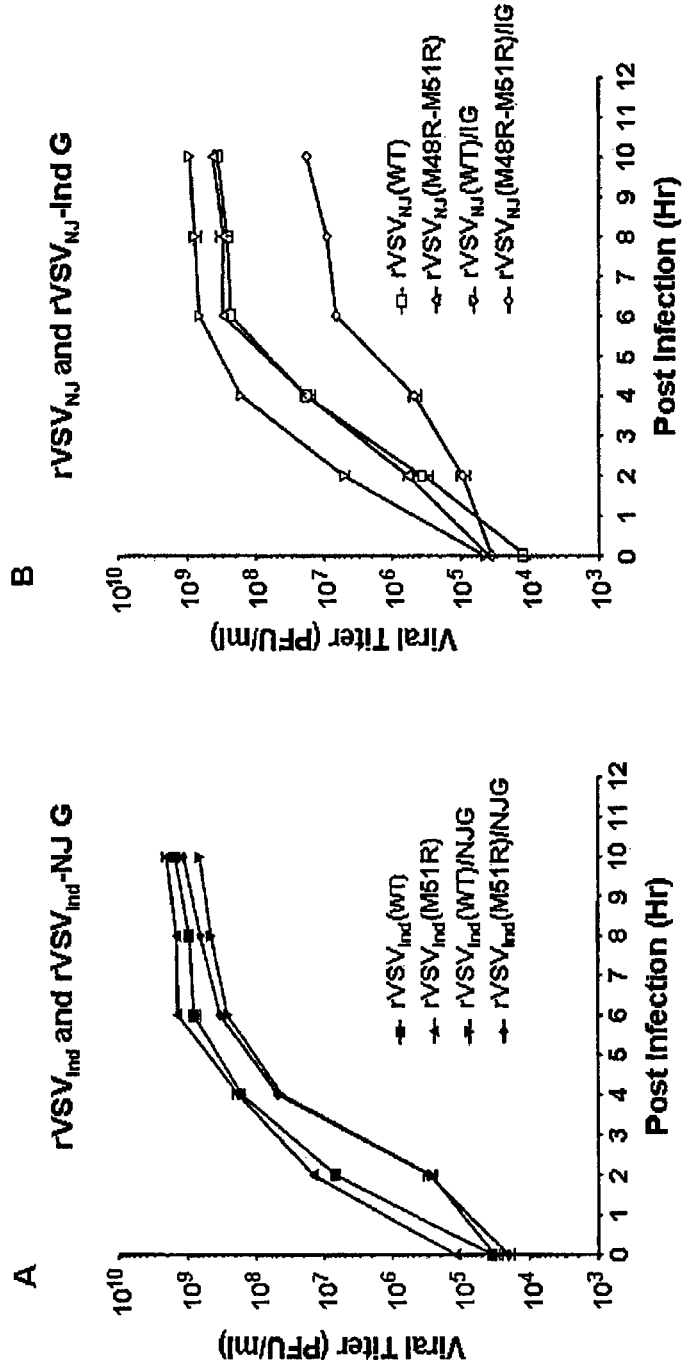
FIG. 3 illustrates growth kinetics of recombinant VSVs without gene of interests.

With reference to FIG. 3, the recombinant VSV were purified by 3 consecutive plaque picking and amplified in baby hamster kidney cells. In order to determine the replication kinetics of the recombinant VSVs, we infected BHT cells with a multiplicity of infection (MOI) of 3 and harvested the cell culture medium from the infected cells every 2 hrs until 10 hrs after infection. Viral titre in the harvested culture medium was determined by plaque assay.

Example 2

Figure 4:
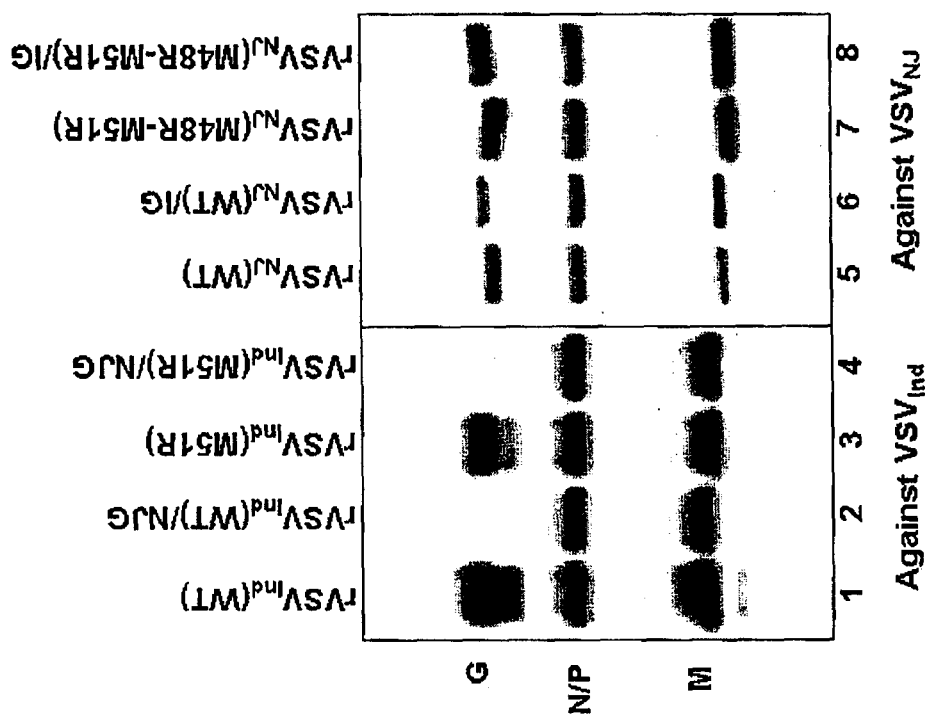
FIG. 4 illustrates expression of VSV proteins in the baby hamster kidney cells infected with recombinant VSVs.
Figure 5:
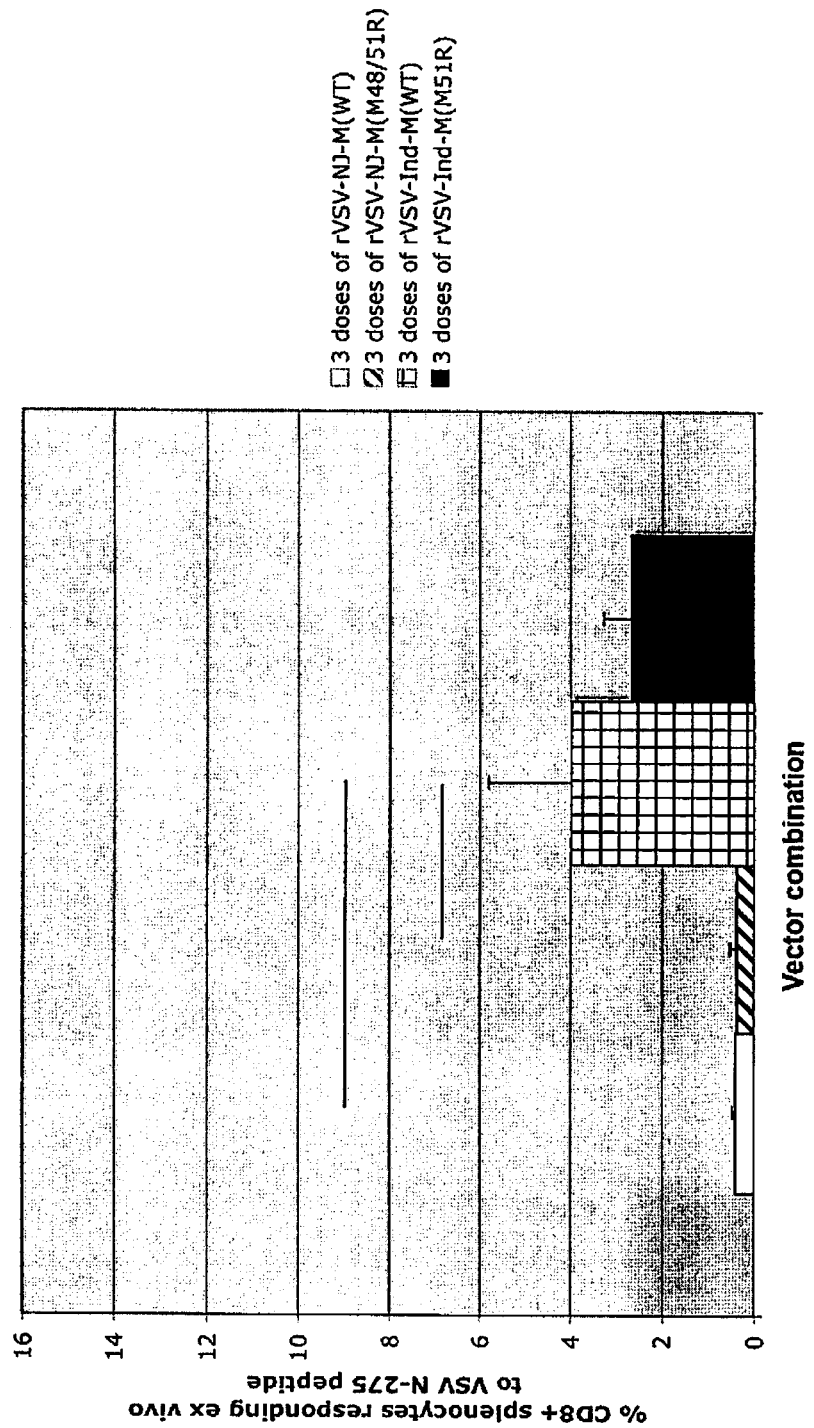
FIG. 5 depicts VSV peptide specific CD8+ T cell responses in Balb/c mice receiving a single virus, 3 dose schedule VSV vaccines.

Expression of VSV Proteins in Baby Hamster Kidney Cells Infected with Recombinant VSVs Expression of proteins from the recombinant VSVs (two serotypes, $VSV_{Ind}$ and $VSV_{NJ}$, VSVs of M wild type and M mutant, and VSVs with G gene switched) was examined by Western blot analysis using antibodies against $VSV_{Ind}$ and $VSV_{NJ}$. Our antibodies against $VSV_{Ind}$ or $VSV_{NJ}$ detect four proteins of VSV (N, P, M, and G). FIG. 4 shows 3 protein bands, because N protein and P protein migrate as the same size proteins on the SDS-PAGE gel.

Antibody against $VSV_{Ind}$ or $VSV_{NJ}$ could detect all four proteins of VSV, N, P, M, and G that were expressed from a single serotype. Exchange of G gene in the $VSV_{Ind}$ NJG was confirmed by the lack of G protein detection by $VSV_{Ind}$ antibody because $VSV_{Ind}$ antibody does not cross-react with the G protein of $VSV_{NJ}$ (lanes 2 and 4). Exchange of G gene in the $VSV_{NJ}$ IG was confirmed by the size differences in $VSV_{Ind}$ G and $VSV_{NJ}$ G. $VSV_{Ind}$ G migrates slightly slower than the G of $VSV_{NJ}$, which is shown on the lane 6 and 8. Mutation in the M gene (M51R in the $VSV_{Ind}$ M protein and M48R-M51R in the $VSV_{NJ}$ M protein) makes M proteins migrate slightly faster than the wild type M proteins of both serotypes, which are demonstrated in lanes 3, 4, 7, and 8. The migration pattern of the M proteins confirms the mutation in the mutant VSVs.

Example 3

Vaccinations Regimens or Schemes to Find Best Combination of Viral Inoculation

With reference to FIGS. 5-8 and Table 1, since an objective of the Applicant is to utilize a prime and boost regimen for immunizing animals, the Applicant determined the best order of recombinant VSV serotypes for the prime and boost immunization scheme. The Applicant studied whether vaccination with 1) vectors based on two different serotypes ($VSV_{Ind}$ or $VSV_{NJ}$), 2) VSV vectors expressing the G protein of the alternate serotype or 3) cytotoxic wild type or non-cytopathic mutant VSV M protein provided any advantage to the generation of VSV specific CD8+ T cells. Table 1 illustrates all possible serotype combinations.

Mice groups were vaccinated with rVSVs in three doses vaccination schedule. In this vaccination study consisting of 13 groups of mice, the objective was to determine the recombinant VSV vaccine construct(s) that generated the highest percentage of VSV nucleocapsid specific CD8+ T cells, based on interferon gamma (IFNγ) production following stimulation with VSV N peptide, VSV N275 (MHC I H2d specific peptide targeted to amino acid sequence in VSV N). In particular, we studied whether vaccination with (1) vectors based 2 different strains ($VSV_{Ind}$ or $VSV_{NJ}$), (2) vectors expressing the G protein of the alternate serotype or (3) cytotoxic wild type or non-cytopathic mutant VSV M protein provided any advantage to the generation of VSV N specific CD8+ T cells.

Six 6-week-old female Balb/c mice (MHC type H2d) per group received 1×10⁶ pfu (plaque forming unit) rVSV for dose 1, administered by intramuscular injection into the posterior thigh muscle and diluted in a total volume of 50 µl PBS. Mice received 1×10⁶ pfu rVSV for the dose 2 and 5×10⁶ rVSV for the dose 3. A time period of 4 weeks separated doses 1 and 2, and an additional 10 weeks separated doses 2 and 3. Mice were euthanized 7 days following the 3$^{rd}$ dose and splenocytes harvested for detection of CD8+ T cells specific to a VSV nucleocapsid peptide (VSV N275).

A single cell suspension of splenocytes was prepared in complete RPMI and then 1×10⁶ cells were transferred to appropriate wells in a U-bottom 96 well plate. VSV N specific peptide VSV N275, NH2-MPYLIDFGL-COOH (GenScript Corporation, Piscataway N.J.) and co-stimulant anti-CD28 (clone 37.51, BD Biosciences, San Jose Calif.) mixtures were added and mixtures incubated for 2 hours. Brefeldin A (BD Biosciences) was added according to the manufacturer's instructions to block cytokine secretion and cells incubated for an additional 3 hours. Cells were stained with antibodies recognizing murine CD8 (FITC-CD8a, 8D Biosciences clone 53-6.7), or appropriate isotype control antibodies. Cells were washed and then permeabilized with Cytofix/cytoperm kit reagents (BD Biosciences) according to the manufacturer's instructions and then stained for IFNγ (APC-IFN γ, BD Biosciences, clone XMG1.2). The stained cells were identified using a FACS Calibur flow cytometer (BD Biosciences) and FlowJo software (Tree Star Inc., Ashland Oreg.). The data is expressed as the average % CD8+IFNγ+ splenocytes in 4-6 mice per group (+/−standard error of the mean, SEM) for each vaccine. Statistical significant was determined using a one-way ANOVA with a Bonferroni correction (Prism 4.0 software, GraphPad Software Inc., San Diego, Calif.).

Results

Figure 8A:
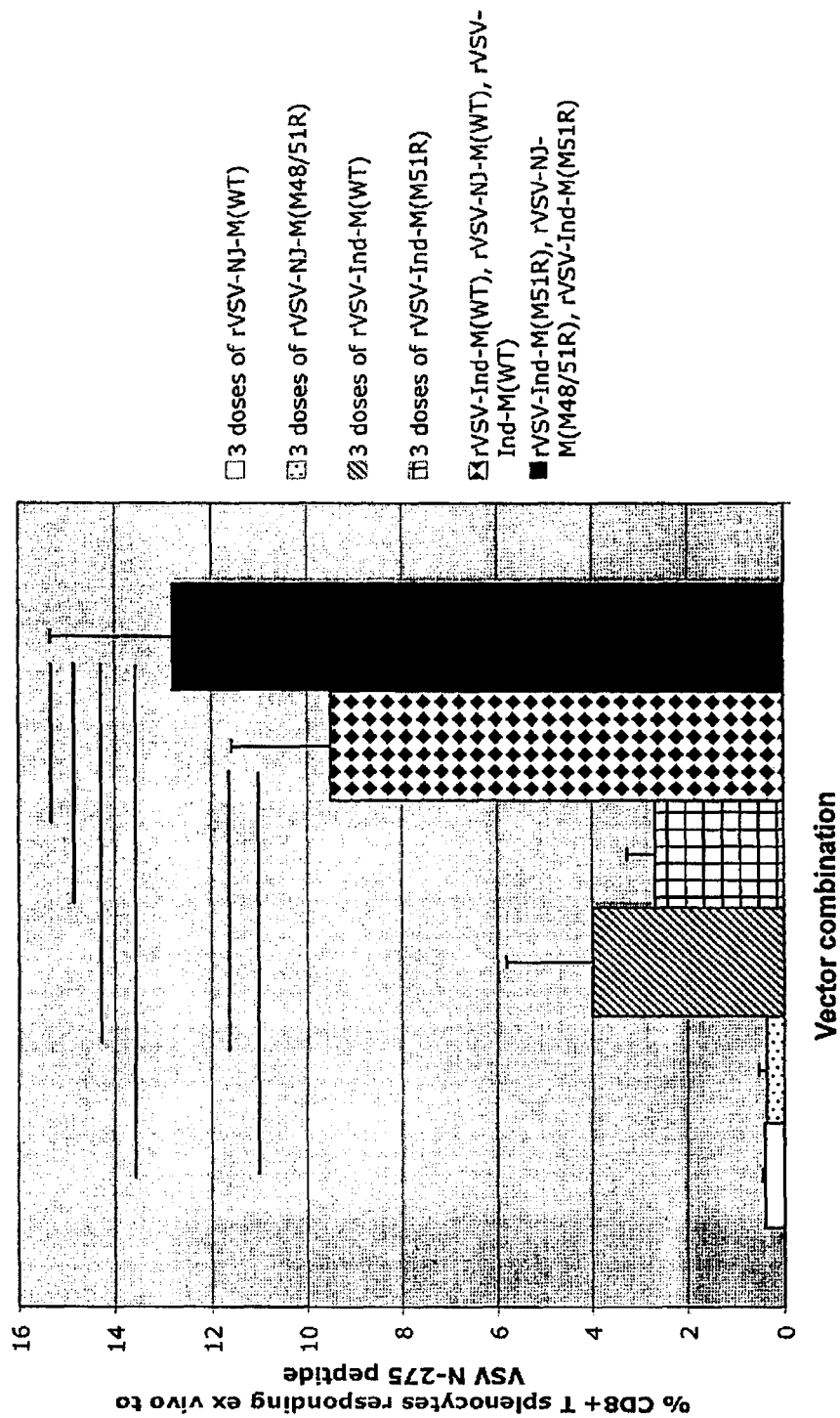
FIG. 8 A depicts the comparisons of VSV peptide specific CD8+ T cell responses in Balb/c mice receiving one or two serotypes of VSV vaccines.
Figure 9:
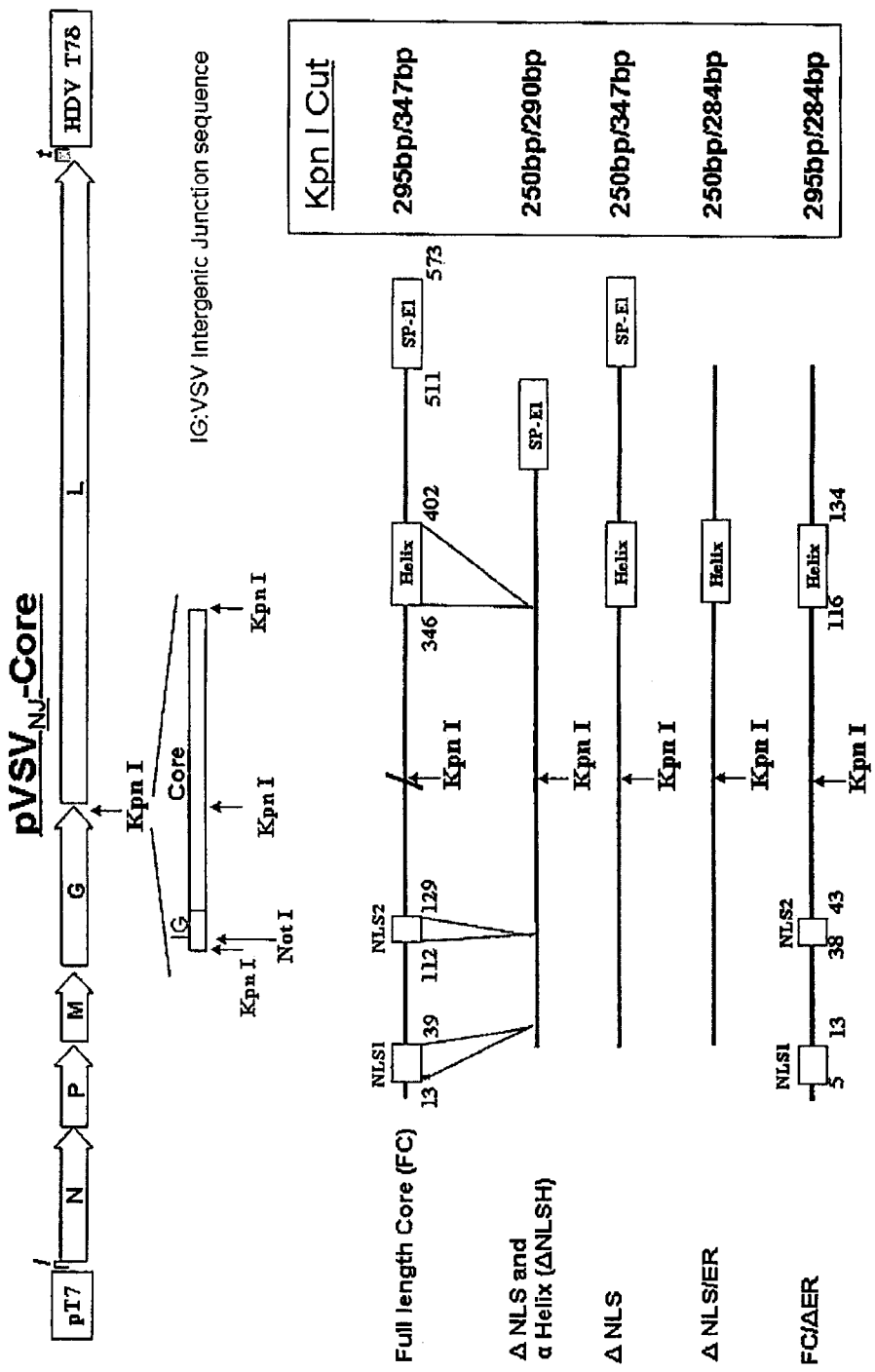
FIG. 9 illustrates the cloning of HCV Core genes with or without deletion mutations into the cDNA clone of $VSV_{NJ}$.
Figure 10:
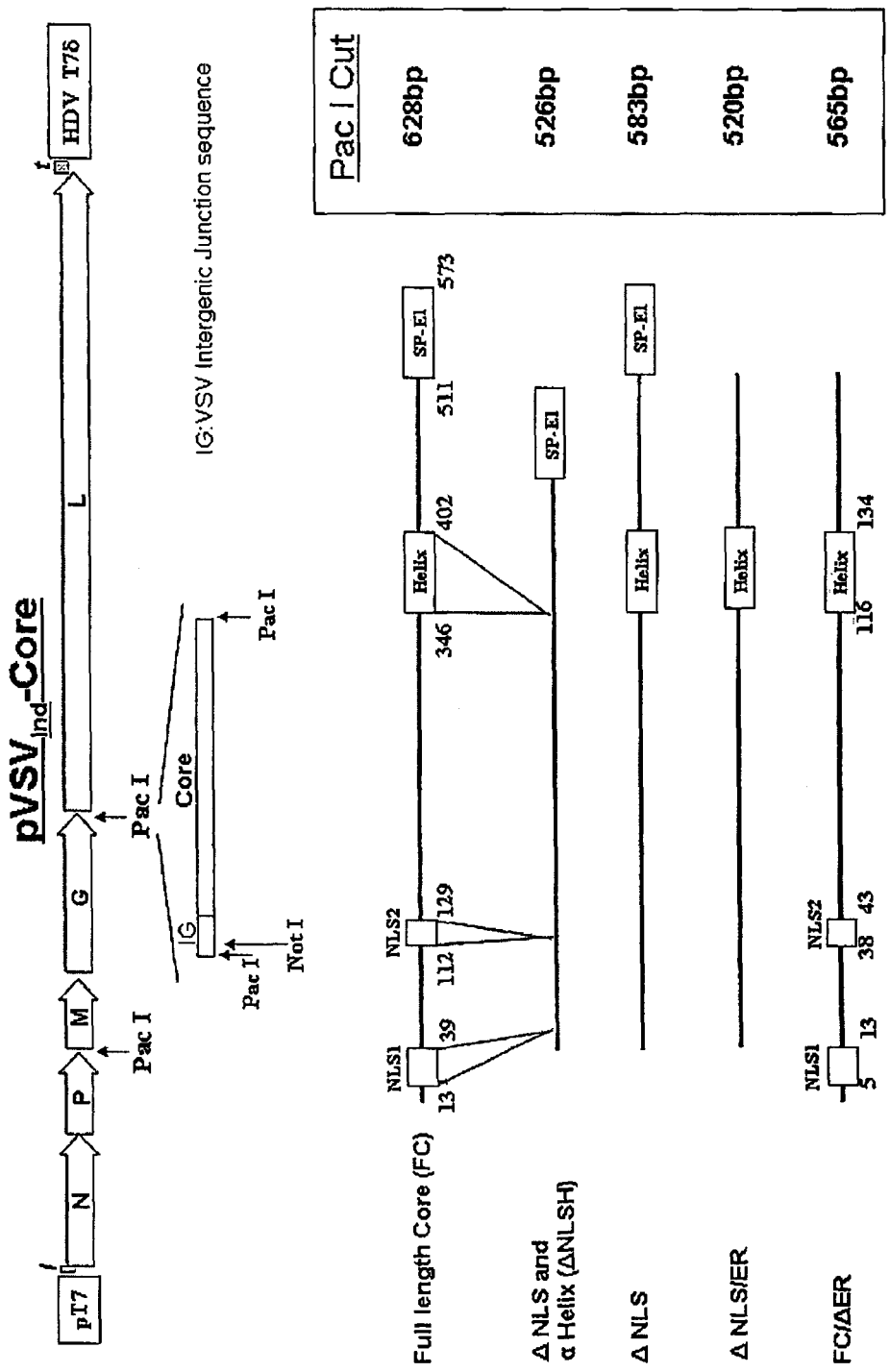
FIG. 10 illustrates the cloning of HCV Core genes with or without deletion mutations into the cDNA clone of $VSV_{Ind}$.
Figure 13:
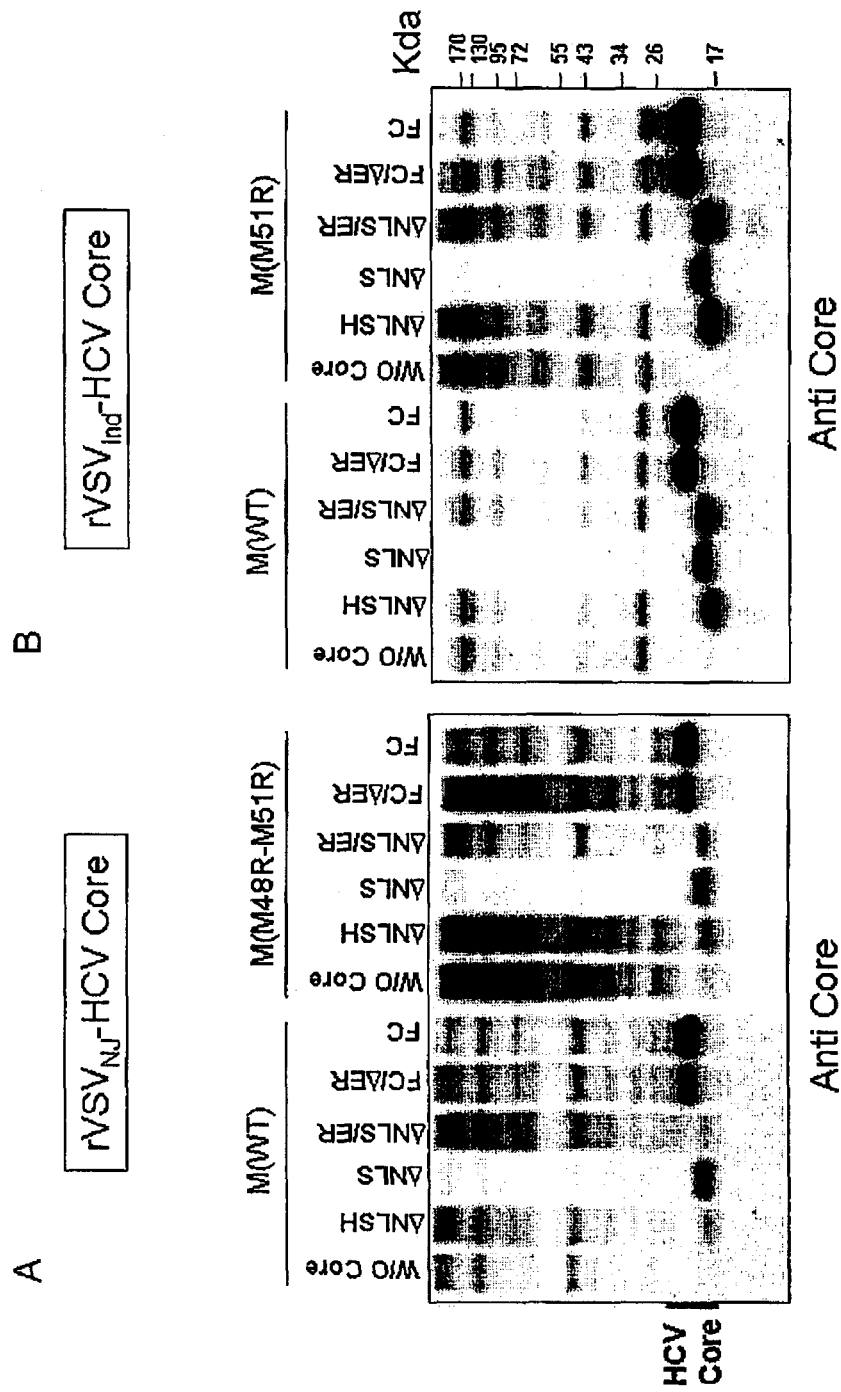
FIG. 13 depicts the expression of HCV Core from the $rVSV_{NJ}$ and $rVSV_{Ind}$ with HCV core genes. HCV core proteins were detected by labelling the infected cell for an hour with 3H-Leu and immunoprecipitating the core protein with antibody against HCV core.
Figure 14:
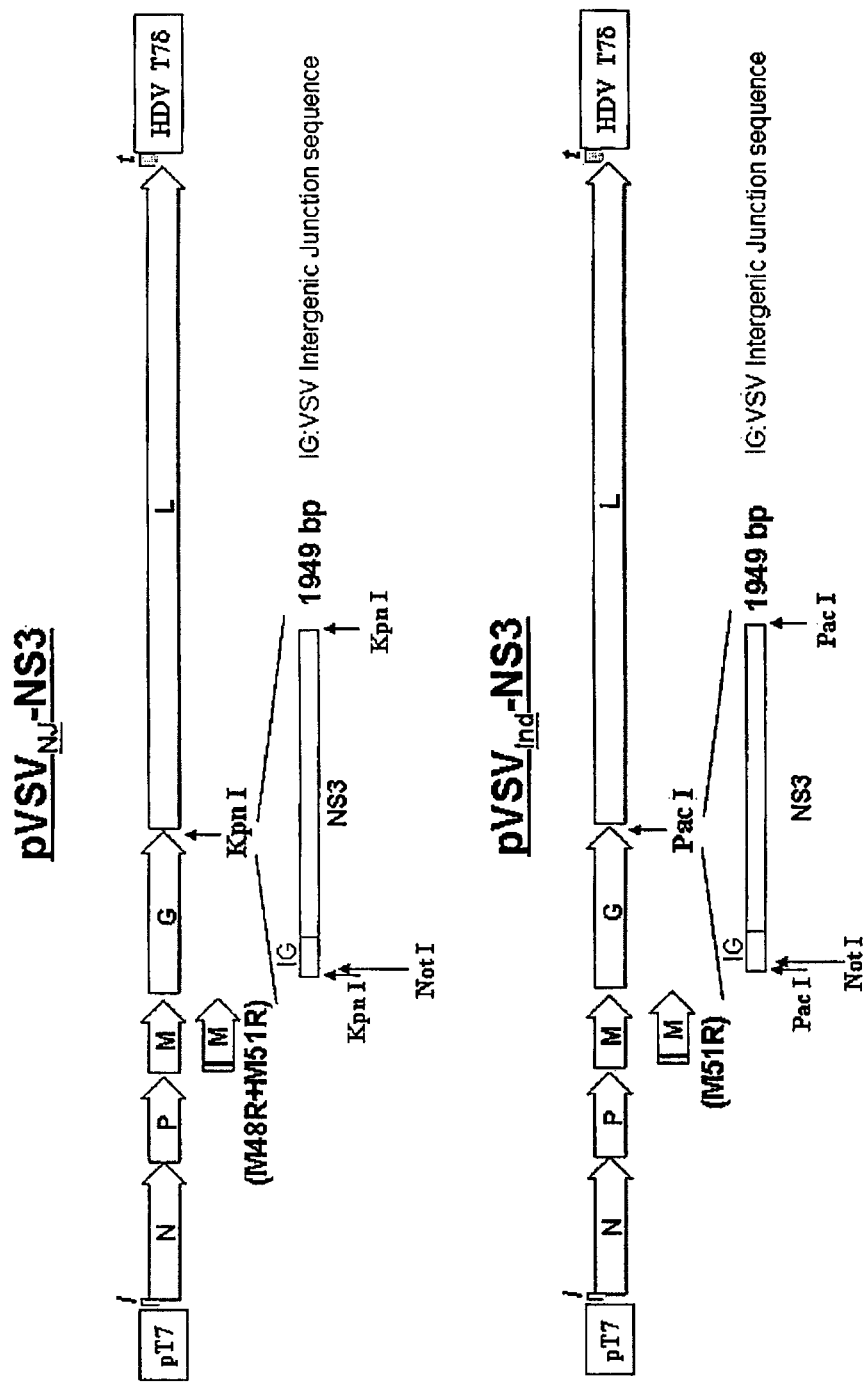
FIG. 14 illustrates the cloning of HCV NS3 genes into the cDNA clone of $rVSV_{NJ}(M_{WT})$, $rVSV_{NJ}(M_{M48R-M51R})$, $rVSV_{Ind}(M_{WT})$, and $rVSV_{Ind}(M_{M51R})$.
Figure 15:
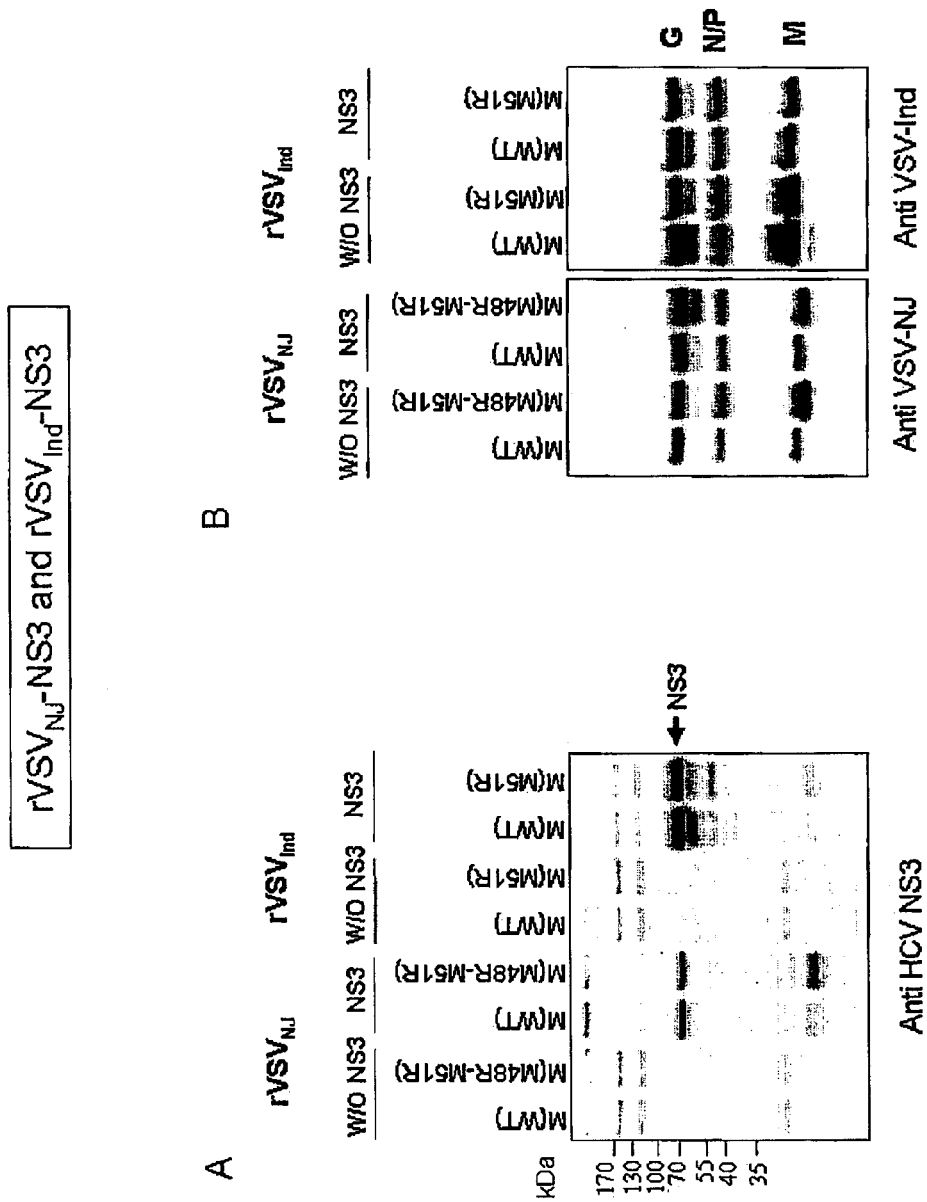
FIG. 15 depicts the recovery of $rVSV_{NJ}(M_{WT})$, $rVSV_{NJ}(M_{m48R-M51R})$, $rVSV_{Ind}(M_{WT})$, and $rVSV_{Ind}(M_{M51R})$ expressing NS3. Expression of NS3, serotypes and M phenotypes of the recovered rVSV was confirmed by Western blot analysis using the HCV NS3 antibody and serotype specific VSV antibodies.
Figure 20:
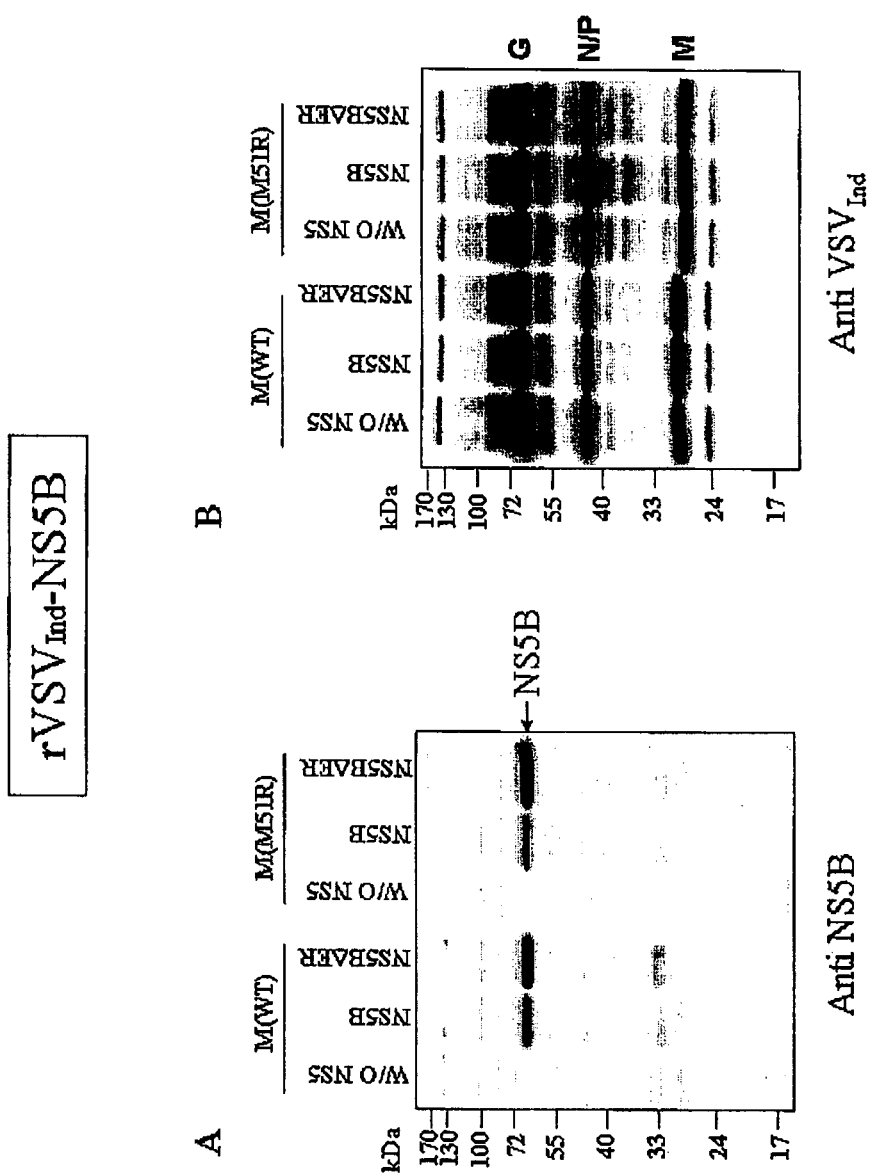
FIG. 20 depicts the recovered $rVSV_{Ind}(M_{WT})$, and $rVSV_{Ind}(M_{m51R})$ expressing NS5B. Expression of NS5B, serotypes and M phenotypes of the recovered rVSV was confirmed by Western blot analysis using the HCV NS5B antibody and serotype specific $VSV_{Ind}$ antibodies.

The results clearly show that alternating the VSV serotypes for the second dose is better than providing three doses of a single VSV serotype for the generation of VSV N specific CD8+ T cells. In view of the results presented herein, a strategy for inducing VSV N specific CD8+ T cells is a first dose of VSV$_{Ind}$-mutant M, followed by a dose of VSV$_{NJ}$-mutant M, and finally a dose of VSV$_{Ind}$-mutant M (FIG. 8A).

Example 4

Immunization Studies with Recombinant VSV Expressing HCV Proteins

Background

Hepatitis C virus (HCV) is causative agent of Hepatitis C in humans. The number of cases of hepatisis C is estimated to be around 170 million worldwide. Approximately 3% of the world's population is chronically infected by the virus. It is estimated that approximately 3 million people in the United States are chronically infected with HCV, with the majority of infections occurring among people 30 to 50 years of age.

Infection with HCV can be extremely serious. The initial infection may cause no disease or may result in hepatitis accompanied by jaundice; fulminant liver failure is rare. However, most HCV infections become chronic. This chronic infection, although tolerated by some, leads to liver disease, cirrhosis and hepatocellular carcinoma. These chronically infected patients are the source of almost all new infections.

Although the HCV genome has been isolated and sequenced more than a decade ago, no effective vaccine to prevent HCV infection or treat acute or chronic HCV, has been developed.

The ideal HCV vaccine or vaccination strategy will be the one that induces both humoral and cellular immune responses. Accordingly, the novel recombinant VSV immunization strategy developed by the Applicant utilizing two different VSV serotypes, provides for a platform for, obtaining an HCV vaccine system.

Generation of Recombinant VSV Expressing HCV Proteins

With reference to FIGS. 9 to 20, HCV core, NS3, NS5A, and NS5B genes were first cloned into pBluescript II KS vector (Stratagen) in order to introduce VSV intergenic junction sequences, which are involved in the transcriptional termination at the upstream gene and transcriptional reinitiation at the downstream gene of VSV. Full length core and four HCV core genes with deletions at the regions involved in the nuclear localization and anchoring into ER membrane were cloned into pBluscript H KS vector. Full length NS3 gene was cloned into pBluescript II vector without modifications. Full NS5A and NS5B, and NS5A and NS5B with deletions at the ER membrane anchoring region were cloned into pBluescript II KS vector. After confirmation of the correct sequences in each clone, the HCV genes with VSV intergenic junction sequences, except full NS5B, were cut with restriction enzyme, Kpn I and cloned into pVSV$_{NJ}$-M(WT) and pVSV$_{NJ}$-M(M48R-M51R) between G gene and L gene. Pac I cut of HCV genes with VSV intergenic junction sequences were cloned into Pac I site between G and L genes in the pVSV$_{Ind}$-M(WT) and pVSV$_{Ind}$-M(M51R). Full NS5B were cut with Spe I from the pBluescript II vector and blunt ended with klenow fragment and ligated to pVSV$_{NJ}$, which was cut with Kpn I and blunt ended with klenow fragment. The insertion of NS5B into pVSV$_{NJ}$ was confirmed by digesting the plasmid with Pac I, which site was introduced to both ends of NS5B clone. HCV Core genes were partially digested with Kpn I because of the presence of one additional Kpn I site in the core gene. The same clones in the pBluescript II vector were cut with restriction enzyme, Pac I in order to clone HCV genes, Core, NS3, NS5A, and NS5B into pVSV$_{Ind}$-M(WT) and pVSV$_{Ind}$-M(M51R). Insertion of HCV genes into the pVSVs were confirmed by digesting the plasmids with Kpn I or Pac I and by DNA sequencing.

Recombinant VSV$_{Ind}$ and VSV$_{NJ}$ expressing HCV Core (FIGS. 11, 12 and 13), NS3 (FIG. 15), NS5A (FIGS. 17 and 18), and NSSB (FIGS. 19 and 20) were recovered from cDNA clones by VSV reverse genetics. The recombinant viruses were purified by three consecutive plaque picking and amplified by infecting BHK cells with a multiplicity of infection (MOI) of 0.1. The expression of HCV proteins from the viruses were determined by Western blot analysis using virus infected cell lysates and antisera against each HCV proteins. Western blot analysis of the same cell lysates using antisera against VSV$_{Ind}$ and VSV$_{NJ}$ determined the serotype and M gene phenotype of the VSV vector expressing each HCV protein. Mutated M proteins of VSV$_{Ind}$(M$_{M51R}$) and VSV$_{NJ}$ (M$_{M48R-M51R}$) migrate slightly faster than wild type M proteins on the SDS-PAGE gel.

Results

Figure 8B:
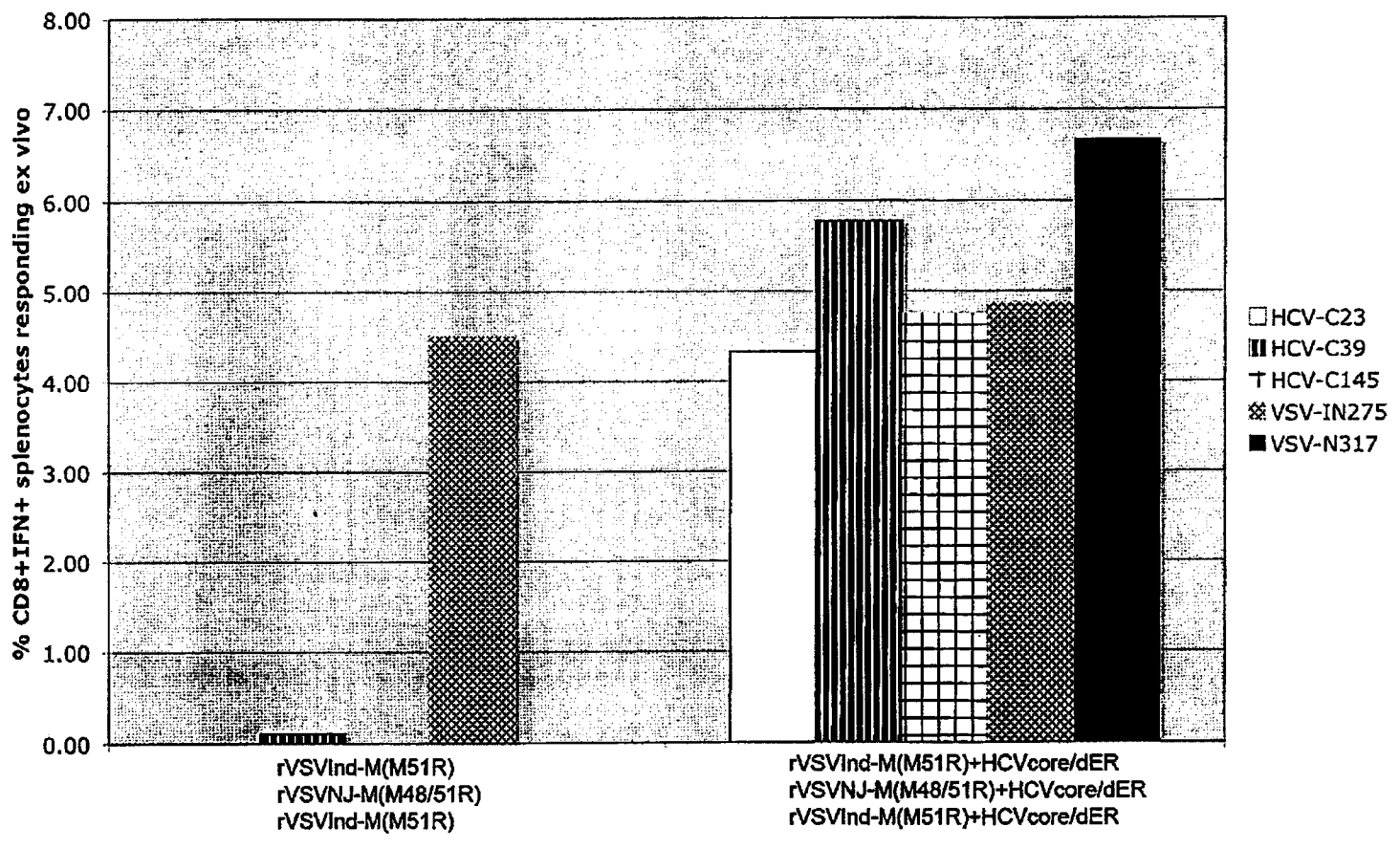

With reference to FIG. 8B, vigorous re-activation of CD8+ T cells was observed following ex vivo stimulation with HCV MHC class I peptides in a cohort of mice (n=2) vaccinated with VSV Ind-M$_{M51R}$+HCV-CoreΔER, then VSV NJ-M$_{M48/51R}$+HCV-CoreΔER, followed 3 weeks later by an additional dose of VSV Ind-M$_{M51R}$+HCV-CoreΔER. This reactivation was shown to be specific for HCV peptides since a control mouse immunized with the VSV vector alone did not exhibit CD8+ T cells specific for HCV peptides (set of bars on left of panel). The reactivation of CD8+ T cells specific for 2 VSV nucleocapsid epitopes was used as positive control in all mice.

human immunodeficiency virus, West Nile virus, hantavirus, influenza virus, dengue hemorrhagic fever virus, Japanese encephalitis virus, and SARS coronavirus.

TABLE 1

Vaccinations to find best combinations of viral inoculation to induce strongest immune responses in mice

| Group ID # | Dose 1 (1 × 10⁶ pfu/mouse, IM) | Dose 2 (4 wks after Dose 1, 1 × 10⁶ pfu/mouse, IM) | Dose 3 (10 wks after Dose 2, 5 × 10⁶ pfu/mouse, IM) | # of Animals |
|---|---|---|---|---|
| 1-0 | PBS | PBS | PBS | 6 |
| 1-1 | rVSVNJ-M(WT) | rVSVNJ-M(WT) | rVSVNJ-M(WT) | 6 |
| 1-2 | rVSVNJ-M(M48R-M51R) | rVSVNJ-M(M48R-M51R) | rVSVNJ-M(M48R-M51R) | 6 |
| 1-3 | rVSVInd-M(WT) | rVSVInd-M(WT) | rVSVInd-M(WT) | 6 |
| 1-4 | rVSVInd-M(M51R) | rVSVInd-M(M51R) | rVSVInd-M(M51R) | 6 |
| 1-5 | rVSVNJ-M(WT) | rVSVInd-M(WT) | rVSVNJ-M(WT) | 6 |
| 1-6 | rVSVNJ-M(M48R-M51R) | rVSVInd-M(M51R) | rVSVNJ-M(M48R-M51R) | 2 + 6 |
| 1-7 | rVSVInd-M(WT) | rVSVNJ-M(WT) | rVSVInd-M(WT) | 6 |
| 1-8 | rVSVInd-M(M51R) | rVSVNJ-M(M48R-M51R) | rVSVInd-M(M51R) | 6 |
| 1-9 | rVSVNJ-M(WT) | rVSVNJ-M(WT)/Ind G | rVSVNJ-M(WT) | 6 |
| 1-10 | rVSVNJ-M(M48R-M51R) | rVSVNJ-M(M48R-M51R)/Ind G | rVSVNJ-M(M48R-M51R) | 6 |
| 1-11 | rVSVInd-M(WT) | rVSVInd-M(WT)/NJ G | rVSVInd-M(WT) | 6 |
| 1-12 | rVSVInd-M(M51R) | rVSVInd-M(M51R)/NJ G | rVSVInd-M(M51R) | 6 |

IM: intramuscularly; Pfu: Plaque forming unit; wks: weeks.

The invention claimed is:

1. A method for preventing or treating an infection caused by a pathogen, said method comprising:
   a) administering to a subject a dose of an effective amount of a first immunogenic composition comprising a full length recombinant vesicular stomatitis virus (rVSV) Indiana serotype (rVSV$_{Ind}$) expressing one or more proteins of the pathogen, and
   b) administering to the subject a dose of an effective amount of a second immunogenic composition comprising a full length rVSV New Jersey serotype (rVSV$_{NJ}$) expressing the one or more proteins of the pathogen;
   wherein the immunogenic composition comprising the rVSV$_{Ind}$ is administered as a prime immunogen and the vaccine comprising the rVSV$_{NJ}$ is administered as a booster immunogen at about 3 weeks, or later, after administration of the prime immunogen;
   wherein the rVSV$_{Ind}$ comprises an Indiana serotype mutant M protein comprising a methionine at position 51 changed to an arginine (M51R substitution), and the rVSV$_{NJ}$ comprises a New Jersey serotype mutant M protein comprising a methionine at position 48 changed to an arginine and a methionine at position 51 changed to an arginine (M48R-M51R substitution); and
   wherein the one or more proteins of the pathogen comprises a B-cell and/or a T-cell epitope.

2. The method of claim 1, wherein said method further comprises:
   c) administering to the subject after the booster vaccine an effective amount of the rVSV$_{NJ}$ immunogenic composition.

3. The method of claim 1 wherein the pathogen is selected from a virus, a bacterium, a fungus and a parasite.

4. The method of claim 1, wherein the pathogen is selected from the group consisting of hepatitis C virus, Ebola virus, 5. A method for inducing an immune response in a subject to a pathogen wherein the method comprises the following steps:
   a) administering to a subject a dose of an effective amount of a first immunogenic composition comprising a full length recombinant vesicular stomatitis virus (rVSV) Indiana serotype (rVSV$_{Ind}$) expressing one or more proteins of the pathogen, and
   b) administering to the subject a dose of an effective amount of a second immunogenic composition comprising a full length rVSV New Jersey serotype (rVSV$_{NJ}$) expressing the one or more proteins of the pathogen;
   wherein the immunogenic composition comprising the rVSV$_{Ind}$ is administered as a prime immunogen and the immunogenic composition comprising the rVSV$_{NJ}$ is administered as a booster immunogen at about 3 weeks after administration of the prime immunogen;
   wherein the rVSV$_{Ind}$ comprises an Indiana serotype mutant M protein comprising a methionine at position 51 changed to an arginine (M51R substitution); and the rVSV$_{NJ}$ comprises a New Jersey serotype mutant M protein comprising a methionine at position 48 changed to an arginine and a methionine at position 51 changed to an arginine (M48R-M51R substitution); and
   wherein the one or more proteins of the pathogen comprises a B-cell and/or a T-cell epitope.

6. The method of claim 5, wherein said method further comprises:
   c) administering to the subject after the booster vaccine an effective amount of the rVSV$_{NJ}$ immunogenic composition.

7. The method of claim 5 wherein the pathogen is selected from a virus, a bacterium, a fungus and a parasite.

8. The method of claim 5, wherein the pathogen is selected from the group consisting of hepatitis C virus, Ebola virus, human immunodeficiency virus, West Nile virus, hantavirus, influenza virus, dengue hemorrhagic fever virus, Japanese encephalitis virus, and SARS coronavirus.

9. A method for preventing or treating an infection caused by a pathogen or for inducing an immune response in a subject to the pathogen, said method comprising:
   a) administering to a subject a dose of an effective amount of a first immunogenic composition comprising a full length recombinant vesicular stomatitis virus (rVSV) New Jersey serotype ($rVSV_{NJ}$) expressing one or more proteins of the pathogen, and
   b) administering to the subject a dose of an effective amount of another immunogenic composition comprising a full length rVSV Indiana serotype ($rVSV_{Ind}$) expressing the one or more proteins of the pathogen;
   wherein the immunogenic composition comprising the $rVSV_{NJ}$ is administered as a prime immunogen and the immunogenic composition comprising the $rVSV_{Ind}$ is administered as a booster immunogen at about 3 weeks after administration of the prime immunogen;
   wherein the $rVSV_{NJ}$ comprises a New Jersey serotype mutant M protein comprising a methionine at position 48 changed to an arginine and a methionine at position 51 changed to an arginine (M48R-M51R substitution), and the $rVSV_{Ind}$ comprises an Indiana serotype mutant M protein comprising a methionine at position 51 changed to an arginine (M51R substitution); and
   wherein the one or more proteins of the pathogen comprises a B-cell and/or a T-cell epitope.

10. The method of claim 9, wherein said method further comprises:
   c) administering to the subject after the booster vaccine an effective amount of the $rVSV_{Ind}$ vaccine or immunogenic composition.

11. The method of claim 9 wherein the pathogen is selected from a virus, a bacterium, a fungus and a parasite.

12. The method of claim 9, wherein the pathogen is selected from the group consisting of hepatitis C virus, Ebola virus, human immunodeficiency virus, West Nile virus, hantavirus, influenza virus, dengue hemorrhagic fever virus, Japanese encephalitis virus, and SARS coronavirus.

* * * * *